United States Patent [19]

Arnold et al.

[11] Patent Number: 5,837,202
[45] Date of Patent: Nov. 17, 1998

[54] METAL CHELATING LIPIDS WHICH ARE USEFUL AS SENSORS IN FLUOROMETRIC METHODS FOR THE DETECTION OF METAL IONS

[75] Inventors: Frances H. Arnold, Pasadena, Calif.; Darryl Y. Sasaki, Albuquerque, N. Mex.

[73] Assignee: California Institute of Technology, Pasadena, Calif.

[21] Appl. No.: 712,193

[22] Filed: Sep. 11, 1996

Related U.S. Application Data

[62] Division of Ser. No. 342,369, Nov. 18, 1994, Pat. No. 5,616,790.

[51] Int. Cl.$^6$ .................. G01N 21/64; C07C 229/34; C07D 255/02
[52] U.S. Cl. .................. 422/82.08; 562/444; 540/474
[58] Field of Search ................. 562/444; 540/474; 422/82.08

[56] References Cited

U.S. PATENT DOCUMENTS

| | | | |
|---|---|---|---|
| 3,855,286 | 12/1974 | Baccini et al. | 260/519 |
| 4,017,596 | 4/1977 | Loberg et al. | 424/1 |
| 4,168,265 | 9/1979 | Tabushi et al. | 260/239 |
| 4,174,428 | 11/1979 | Tabushi et al. | 525/334 |
| 5,132,095 | 7/1992 | Koshiishi et al. | 422/82.07 |
| 5,405,975 | 4/1995 | Kuhn et al. | 549/347 |
| 5,496,522 | 3/1996 | Vo-Dinh et al. | 422/82.05 |

OTHER PUBLICATIONS

Shaffar et al., "Optical Sensors: Part 23* Effect of Langmuir–Blodgett Layer Composition on the Response of Ion-selective Optrodes for Potassium Based on the Fluorimetric Measurement of Membrane Potential," *Analyst*, vol. 113, pp. 693–697, May 1988.

Shimomura et al., "Interaction of Ions with Surface Receptor of the Azobenzene–Containing Bilayer Membrane. Discrimination, Transduction, and Amplification of Chemical Signals," *J. Am. Chem. Soc.* 1982, 104, 1757–1759.

Singh etal., "Metal Ion Induced Phase Changes in Self–Assembled Membranes," *Langmuir* 1992, 8, 1570–1577.

Caminati et al., "Langmuir–Blodgett films of alkylpyridines as metal ion sensors," *Thin Solid Films*, 244 (1994) 905–908.

Morrison et al., 1973, Organic Chemistry, Allyn and Bacon, Inc., Boston, p. 86.

*Primary Examiner*—Donald E. Adams
*Assistant Examiner*—Jeffrey S. Parkin
*Attorney, Agent, or Firm*—Oppenheimer Wolff & Donnelly LLP

[57] ABSTRACT

An fluorescent metal-chelating amphiphile having the structure:

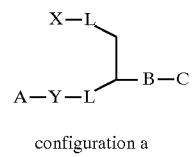

configuration a or

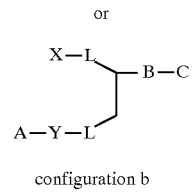

configuration b wherein A is a hydrophobic fluorophore, X and Y are aliphatic hydrocarbons having from 9 to 25 carbon atoms, B is a hydrophilic spacer, C is a metal chelator, and L is either an ether or ester linkage.

The fluorescent metal-chelating amphiphile is combined with a matrix lipid to form lipid-based sensors which provide fluorometric detection of metal ions in liquids.

12 Claims, 16 Drawing Sheets

METAL CHELATING LIPIDS WHICH ARE USEFUL AS SENSORS IN FLUOROMETRIC METHODS FOR THE DETECTION OF METAL IONS

This is a divisional of application(s) Ser. No. 08/342,369 filed on Nov. 18, 1994, now U.S. Pat. No. 5,616,790. +gi The U.S. Government has certain rights in this invention pursuant to Grant No. N00014-92-J-1178 awarded by the United States Navy.

BACKGROUND OF THE INVENTION

1. Field of the Invention

The present invention relates generally to sensors that are used to detect and measure the presence of metal ions in solutions. More particularly, the present invention is directed to metal chelating lipids which are useful as sensors in fluorometric methods for detecting metal ions.

2. Description of Related Art

The detection of metal ions is an important area of analytical chemistry. A multitude of procedures and instruments is available for measuring a wide variety of metal ions, including copper, iron, lead, cadmium, mercury, nickel, cobalt, calcium and potassium. Many of these methods, however, depend upon highly specialized sensors to provide adequate levels of specificity and sensitivity. For example, flow injection atomic absorption spectrometry and size exclusion chromatography followed by inductively coupled plasma mass spectrometry (SEC/ICP-MS) are capable of detecting minute quantities of a wide variety of metal ions. However, such detection systems are very expensive to build and operate. In addition, the instrumentation is often very large and delicate and thus is restricted to use in a controlled laboratory environment. Other commonly used sensors, such as ion-selective electrodes (ISE), ion-selective field effect transistors (ISFET) and chemically modified field effect transistors (CHEMFET), are more convenient to use but are usually specific for a single metal ion, often lack high sensitivity, and require complex schemes for their manufacture.

Fluorimetry is an analytical method which has been used both to quantitatively and qualitatively detect metal ions. Fluorimetry is based on the ability of various molecular species (fluorophores) to absorb a photon of a particular energy (wavelength) and subsequently emit a second photon of lower energy (longer wavelength). The wavelength and intensity of the emitted light are often highly dependent on the chemical environment surrounding the fluorophore. Changes in the fluorescence emission properties of the fluorophore due to the presence of metal ions can be used to provide a measure of the ion concentration. An advantage of fluorimetric detection methods is that they are, in general, extremely sensitive.

An example of a fluorimetric sensing technique is fluorescent photoinduced electron transfer [PET; see Bissell et al., "Fluorescent PET (Photoinduced Electron Transfer) Sensors," Topics in Current Chemistry, 168 (1993), pp. 223–264]. In such a sensor, the detector molecule consists of a fluorophore that is linked by a spacer to an ion-binding receptor. Upon absorption of a photon the detector molecule can release the energy via either fluorescence or electron transfer. Binding of ions by the receptor perturbs the competition between these two processes and thus affects the intensity of light emitted.

Fluorescently-labeled synthetic lipids have been investigated recently for use in a variety of metal ion sensor systems. Lipids possess the ability to self-assemble into different structures (e.g. vesicle bilayers, monolayers, Langmuir-Blodgett (LB) multilayers, etc.), and thus are convenient starting materials for construction of a sensor. An exemplary lipid-based sensor for the detection of potassium ions is disclosed in an article written by Schaffer et al. entitled "Optical Sensors-Part 23. Effect of Langmuir-Blodgett Layer Composition on the Response of Ion-Selective Optrodes for Potassium, Based on the Fluorimetric Measurement of Membrane Potential" (Analyst, May 1989, Vol. 113, pp. 693–697). This sensor consists of a composite four layer LB film deposited onto a glass support. The bottom two layers, nearest the glass surface, consist of the neutral ion-carrier peptide, valinomycin, and an inert matrix fatty acid, arachidic acid. The top two layers, exposed to the surrounding medium, are composed of a lipid-linked fluorescent dye, rhodamine B, and arachidic acid. Valinomycin serves to concentrate the potassium ($K^+$) ions near the lipid-water interface. The emission intensity of rhodamine in the lipid layer is strongly dependent upon the membrane potential between an aqueous sample solution and the lipid phase. The potential is in turn dependent upon the potassium concentration in the sample solution. Thus, the fluorescence intensity was found to decrease with increasing $K^+$ concentration. The change in intensity was found to be linear with $K^+$ concentration over the range 0.01–100 mM, and the selectivity factor for $K^+$ over $Na^+$, a common interfering ion, was $10^4$.

A second example of an ion sensor based on lipid LB films was described by W. Budach, et al. ("Metal Ion Sensor Based on Dioctadecyl-dithiocarbamate-Metal Complex Induced Energy Transfer, " Thin Solid Films 210/211 (1992), pp. 434–436). This sensor also consists of four lipid layers on a glass support as follows: a hydrophobic anchor layer of eicosyl amine; a mixed layer of arachidic acid, arachidic methyl ester, and the fluorophore, N,N'-dioctadecyl-oxacyanine perchlorate (S9); a spacer layer of arachidic acid; and the metal ion-binding layer, dioctadecyldithiocarbamate (DOTC), which is exposed to the aqueous solution. The fluorescence emission spectrum of the dye shows significant overlap with the absorption spectrum of the Cu-DOTC complex. Thus, in the presence of $Cu^{2+}$ some fraction of the excited dye molecules will relax to the ground state via energy transfer to the Cu-DOTC complex rather than via fluorescence, and a decrease in the emission intensity is observed. This sensor was incorporated into a flow cell and found to have a sub-micromolar detection limit for $Cu^{2+}$ and a response time of only a few seconds.

While LB films have the advantage of forming well-ordered, two-dimensional architectures which are highly desired in many sensors, they suffer from a lack of stability and are difficult to produce in large quantities. Lipid bilayer vesicles, in contrast, are relatively simple to prepare, even in large quantities, and thus are an attractive framework on which to build a sensing device. Like LB films, lipid bilayer vesicles are spontaneously assembled from their lipid components to yield a degree of organization not easily accessible with other types of molecules. An example of a metal ion sensor based on lipid vesicles and UV absorbance (not fluorimetry) has been described by Shimomura and Kunitake ("Interaction of Ions with the Surface Receptor of the Azobenzene-Containing Bilayer Membrane. Discrimination, Transduction, and Amplification of Chemical Signals," J. Am. Chem. Soc. 104 (1982), pp. 1757–1759). This simple system consists of two lipids, an azobenzene-containing dye lipid with a metal-binding ethylenediamine headgroup and a matrix lipid, dioctadecyl dimethylammonium bromide (DODAB), co-sonicated to form mixed-lipid bilayer vesicles. At low pH the dye lipid headgroup is positively charged and the lipid is dispersed throughout the bilayer exhibiting an absorbance maximum at 355 nm. When a divalent anion such as $SO_4^{2-}$ is added, the anion can bridge the positively charged headgroups of the dye lipid causing aggregation of the dye and a concomitant hypsochromic shift of the absorbance to 312 nm. If the same dye is mixed with a slightly different matrix lipid which inhibits aggregation of the dye lipid at neutral pH (where the headgroup is unprotonated), the monomer absorbance is again observed at 355 nm. When $Cu^{2+}$ is added to the solution, chelation of the metal ion by the dye headgroup results in a new absorption maximum of the azobenzene cluster at 312 nm.

Recently, an improvement on this system has been reported by Singh, et al. ("Metal Ion Induced Phase Changes in Self-Assembled Membranes," Langmuir 8 (1992), pp. 1570–1577) in which the amine head group of the azobenzene dye was replaced with cyclam, a strong chelator for $Cu^{2+}$. This cyclam azobenzene amphiphile (CABA) and a similar ammonium bromide matrix lipid (1:30 molar ratio) were formed into mixed bilayer vesicles. CABA was found to be dispersed as the isolated species within the fluid matrix above 24.5° C., with an absorbance maximum at 360 nm. At temperatures in the range 24.5°–45° C., chelation of $Cu^{2+}$ by the cyclam headgroup results in formation of azobenzene dye clusters, which results in a shift in the absorbance from 360 to 320 nm. A linear increase in the absorbance of vesicles at 326 nm with increasing $Cu^{2+}$ concentration in the range of 6–36 $\mu$M was observed.

Although the azobenzene lipid system described above is intriguing due to its simplicity (only two component molecules) and the ease with which it can be produced, several problems remain which make this system unsuitable for production of a practical sensor. First, temperature cycling in the range of 10° to 80° C. was required to allow the necessary phase change to occur. Secondly, the UV wavelength monitored, 326 nm, is well out of the visible spectrum and therefore requires the use of a spectrophotometer and quartz optics. Finally, the restricted range of concentrations measurable (less than an order of magnitude) and the relatively low sensitivity greatly limit its application.

Although a great deal of progress has been made in investigating possible modified lipids for use as detectors, there is still a continuing need to further investigate modified lipids in order to provide improved detectors which are easy to use and have the desirable characteristics mentioned above.

SUMMARY OF THE INVENTION

In accordance with the present invention, a new fluorescent metal-chelating amphiphile has been developed which is particularly well suited for use as an integral part of a lipid-based metal sensor. The fluorescent metal-chelating amphiphile has the structure:

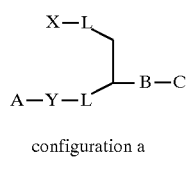

configuration a or

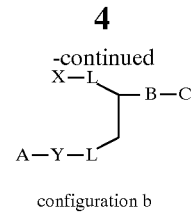

configuration b wherein A is a hydrophobic fluorophore, X and Y are aliphatic hydrocarbons having from 9 to 25 carbon atoms, B is a hydrophilic spacer, C is a metal chelator, and L is either an ether or ester linkage.

The fluorescent metal-chelating amphiphile is composed of a hydrophobic lipid molecule which is labeled with a fluorophore (A) such as pyrene. The fluorophore-labeled lipid molecule is functionalized with a chelating headgroup (C) such as iminodiacetic acid (IDA). The headgroup is connected to the lipid molecule by way of a hydrophilic spacer (B) such as tri(ethylene oxide), $(OCH_2CH_2)_3$. The aliphatic hydrocarbon tails are attached to the backbone via an ether or ester linkage.

When the fluorescent metal-chelating amphiphile is placed in a lipid bilayer of DSPC or other suitable matrix lipid, the fluorophore forms aggregates, as evidenced by a high fluorescent excimer emission intensity. In the presence of various metal ions, the intensity of the excimer emission decreases. Therefore this mixed lipid bilayer system functions as a sensor for metal ions. This dramatic change in the fluorescence excimer emission is believed to be due to dispersion of the initially-aggregated fluorescent metal-chelating amphiphile into the matrix lipid upon metal binding.

As a feature of the present invention, it was discovered that the fluorescent metal-chelating amphiphile of the present invention, when utilizing a pyrene fluorophore and an IDA headgroup, provides a selective detector for copper (II) ions when placed in liposomes of a matrix lipid such as distearoylphosphatidylcholine (DSPC). This particular sensor in accordance with the present invention is capable of selectively detecting copper ions down to at least nanomolar concentrations. In addition, the sensor has relatively rapid response time and is re-usable.

Sensors in accordance with the present invention which are based upon the fluorescent metal-chelating amphiphile are easily prepared by mixing the fluorescent metal-chelating amphiphile lipid with a matrix lipid to form a lipid-based sensor. The lipid-based sensors are relatively rugged and are particularly well-suited for use inside or outside the laboratory. Further, the change in fluorescence which occurs when metal ions are detected is sufficiently dramatic that it can be observed visually under black light, without the need for complex optics or photo detectors, at sufficiently high metal concentrations.

The above discussed and many other features and attendant advantages of the present invention will become better understood by reference to the following detailed description when taken in conjunction with the accompanying drawings.

DETAILED DESCRIPTION OF THE INVENTION

Figure 1:
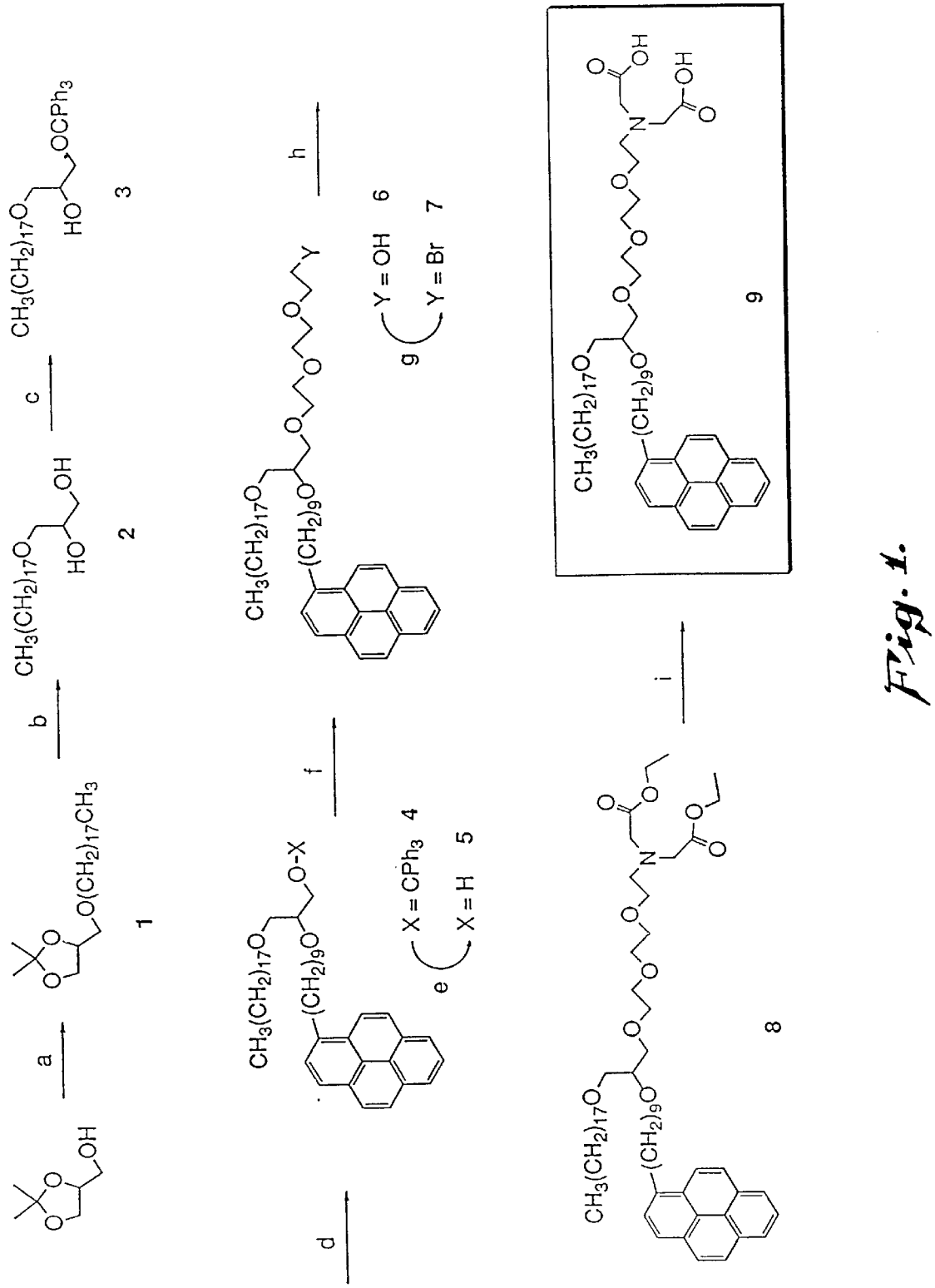
FIG. 1 is a diagram of the synthesis scheme for making an exemplary preferred metal-chelating fluorescent lipid in accordance with the present invention.

In accordance with the present invention, a new fluorescent metal-chelating amphiphile has been developed which is particularly well suited for use as an integral part of a lipid-based metal sensor. The fluorescent metal-chelating amphiphile has the structure:

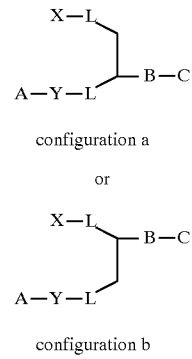

configuration a or configuration b wherein A is a hydrophobic fluorophore, X and Y are aliphatic hydrocarbons having from 9 to 25 carbon atoms, B is a hydrophilic spacer, C is a metal chelator, and L is either an ether or ester linkage.

The fluorescent metal-chelating amphiphile is composed of a hydrophobic lipid molecule which is labeled with a fluorophore (A) such as pyrene. The fluorophore-labeled lipid molecule is functionalized with a chelating headgroup (C) such as iminodiacetic acid (IDA). The headgroup is connected to the lipid molecule by way of a hydrophilic spacer (B) such as tri(ethylene oxide), $(OCH_2CH_2)_3$.

The aliphatic hydrocarbons, designated as X and Y in the above formula, are designed to form a lipid body which is capable of being incorporated within a bilayer liposome or other lipid membrane assembly. The aliphatic hydrocarbon tails are attached to the lipid backbone by either an ether or ester linkage (L). The aliphatic hydrocarbons may have from 9 to 25 carbon atoms. Exemplary aliphatic hydrocarbons include: myristyl, palmityl, stearyl, arachidyl, behenyl and oleyl chains. Fluorescent metal-chelating amphiphiles where X is an aliphatic hydrocarbon having 18 to 20 carbon atoms and Y is an aliphatic hydrocarbon having 9 to 11 carbon atoms are preferred.

Preferred chelating groups (C) include iminodiacetic acid (IDA), cyclam, penicillamine, dimercaptosuccinic acid, tartrate, thiomalic acid, crown ethers, nitrilotriacetic acid (NTA), ethylenediaminetetraacetic acid (EDTA), ethylenebis(oxyethylenenitrilo)tetraacetic acid (EGTA), 3,6-dioxaoctanedithioamide, 3,6-dioxaoctanediamide, salicyladoximine, dithiooxamide, 8-hydroxyquinoline, cupferron, 2,2'-thiobis(ethyl acetoacetate), 2,2'-dipyridyl. IDA is a preferred chelating headgroup which is selective for copper ions.

The chelating headgroup (C) is connected to the lipid backbone by way of a hydrophilic spacer such as ethylene oxide, glycine, cysteine or cysteamine. Preferred hydrophilic spacers (B) include ethylene oxide ($C_nH_{2n}O_n$) where n=2 to 10.

The fluorophore (A) is preferably pyrene, or similar hydrophobic fluorophore such as anthracene, naphthalene, phenanthrene and their derivatives. Pyrene and its derivatives are preferred fluorophores.

The above described fluorescent metal-chelating amphiphiles are prepared in accordance with conventional organic synthesis procedures. An example of a preferred exemplary synthesis is set forth below in Example 1. The particular fluorescent metal-chelating amphiphile which is synthesized is pyrene stearyl iminodiacetic acid (PSIDA) where A is pyrene, X is $CH_3(CH_2)_{17}$, Y is $(CH_2)_9$, B is $(OCH_2CH_2)_3$, L is an ether linkage and C is iminodiacetic acid in configuration a. Other fluorescent metal-chelating amphiphiles can be made in a manner similar to PSIDA by substituting different chelating groups, fluorophores, aliphatic hydrocarbons, and hydrophilic spacers into the synthesis scheme.

The lipid-based metal sensor in accordance with the present invention is prepared by combining the fluorescent metal-chelating amphiphile with an appropriate matrix lipid. A suitable matrix lipid can be found by forming mixed vesicles with the metal-complexing fluorescent amphiphile (5–30 mol %) with the matrix lipid. A suitable matrix lipid will result in aggregation of the metal complexing amphiphile and fluorescent emission at the wavelength of the excimer which will decrease upon metal binding. The optimum matrix lipid will give the largest change in relative fluorescent emission intensity (E/M) upon metal binding at the expected metal concentration. Suitable matrix lipids include distearoylphosphatidylcholine (DSPC), dipalmitoylphosphatidylcholine (DPPC), diarachidoylphosphatidylcholine (DAPC), dibehenoylphosphatidylcholine(DBPC), and distearoylphosphatidic acid (DSPA). While several different matrix lipids could be used, it is not expected that all matrix lipids will be appropriate for all fluorescent metal-chelating amphiphiles. The best combination is found by experimentation, as described above. DPPC and DSPC are preferred lipids.

The fluorescent metal-chelating amphiphile and matrix lipid may be mixed and sonicated to form liposomes or, alternatively, if desired, the matrix lipid/fluorescent metal-chelating amphiphile mixture can be deposited onto a suitable substrate to form a sensor coating. Suitable substrates include glass, quartz, silicon, mica, and these materials coated with gold. The substrate can be in the form of a plate, rods, or sphereswhich can range in surface area from many centimeters clown to a few microns. The relative amount of fluorescent metal-chelating amphiphile which is mixed with the matrix lipid to form the lipid-based sensor should be sufficient to provide a final relative concentration of fluorophore on the order of 1 mole percent to 30 mole percent of the total lipid. The fluorescent metal-chelating amphiphile and matrix lipid are mixed together and treated to form liposomes or lipid-based sensor coatings in accordance with conventional procedures used to form liposomes or deposit lipid layers onto substrates.

Figure 10:
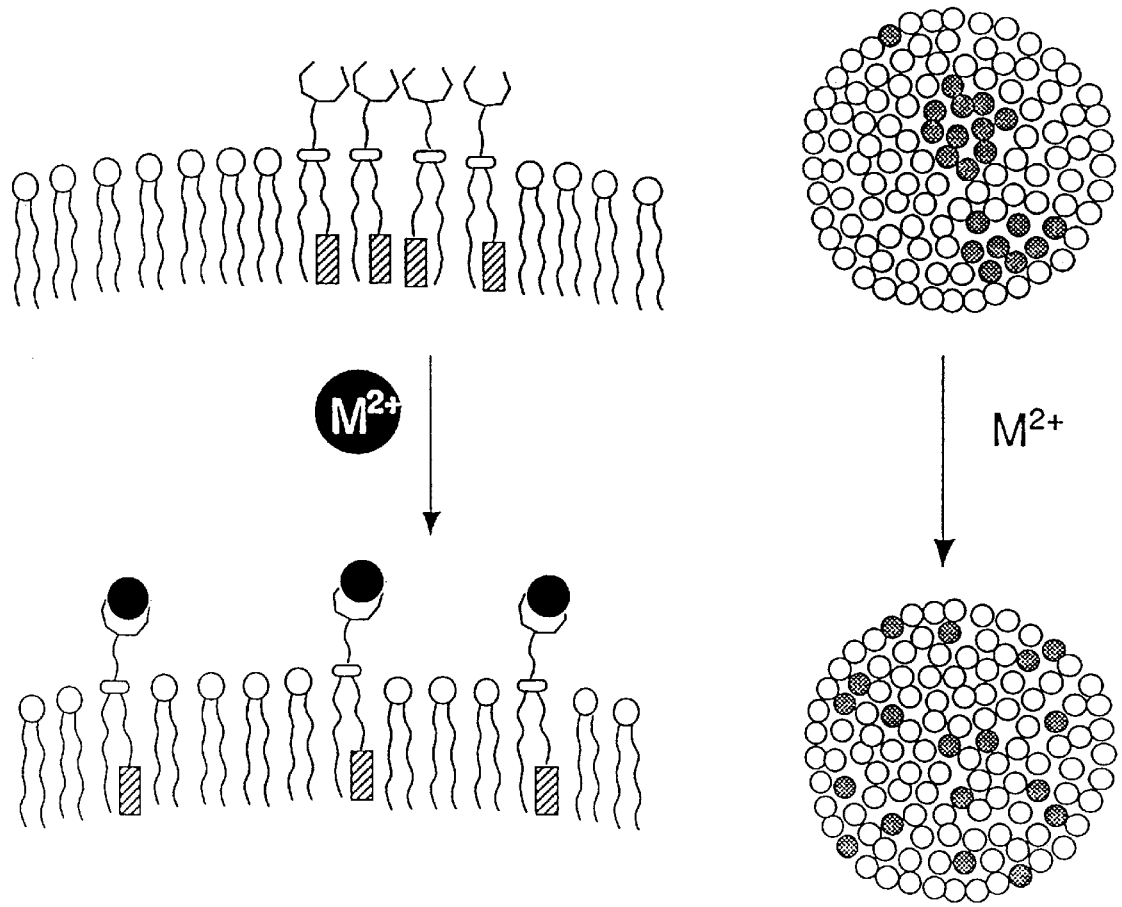
FIG. 10 depicts the believed mechanism of the sensor in accordance with the present invention. At room temperature, the fluorescently-tagged metal-chelating PSIDA lipid is believed to assemble into pyrene-rich domains, which are dispersed upon chelation of a divalent metal ion by the IDA headgroup.

It is believed that the change in fluorescence exhibited by the lipid-based sensors in accordance with the present invention is due to a metal binding-induced dispersion of initially-aggregated fluorescent metal-chelating amphiphiles. A pictorial representation of this sensor mechanism is shown in FIG. 10. On the left side of the figure, a liposome is shown which includes aggregates of fluorescent metal-chelating amphiphiles (shaded circles) located in a matrix of lipid molecules (open circles). Upon addition of a metal ion, such as copper, the chelating lipid undergoes dispersion, which results in the complete mixing of the two lipid components shown on the right side of FIG. 10. The dispersion of the fluorescent metal-chelating amphiphiles results in a change in fluorescence which is easily observed visually or measured by appropriate instrumentation.

The sensor in accordance with the present invention may be made selective for a particular metal ion by choosing an appropriate metal chelator for the amphiphilic fluorophore. The chelator IDA was found to be selective for copper ions. Sensors for other metal ions, such as nickel, calcium, manganese and cobalt may be prepared, if desired, by varying the fluorophore (A), aliphatic hydrocarbon groups (X and Y), hydrophilic spacer (B) and metal chelator (C) and experimentally determining the sensitivity of the fluorescence changes for the particular metal using different matrix lipids. In particular, the matrix lipid, headgroup and solution conditions (e.g. pH) should be chosen such that the metal-chelating amphiphilic fluorophore is aggregated in the absence of the metal ion one wishes to detect. The aggregation is reflected by a relatively large excimer fluorescence. Binding of the metal ion should result in dispersion of the metal-chelating amphiphilic fluorophore into the matrix lipid and a measurable change in the excimer and/or monomer fluorescence intensity.

The lipid-based metal sensor of the present invention can be used in a variety of modes to sense the presence of metal ions and determine their concentrations. In one embodiment, the mixed liposomes (or other appropriate lipid assembly) of the metal-chelating fluorescent amphiphile and matrix lipid are added with an aliquot of the sample solution to a quartz cuvette appropriate for insertion in a fluorescence spectrometer. The concentration of metal ions is determined from the fluorescence intensity, as compared to a reference sample of known metal concentration.

Figure 16:
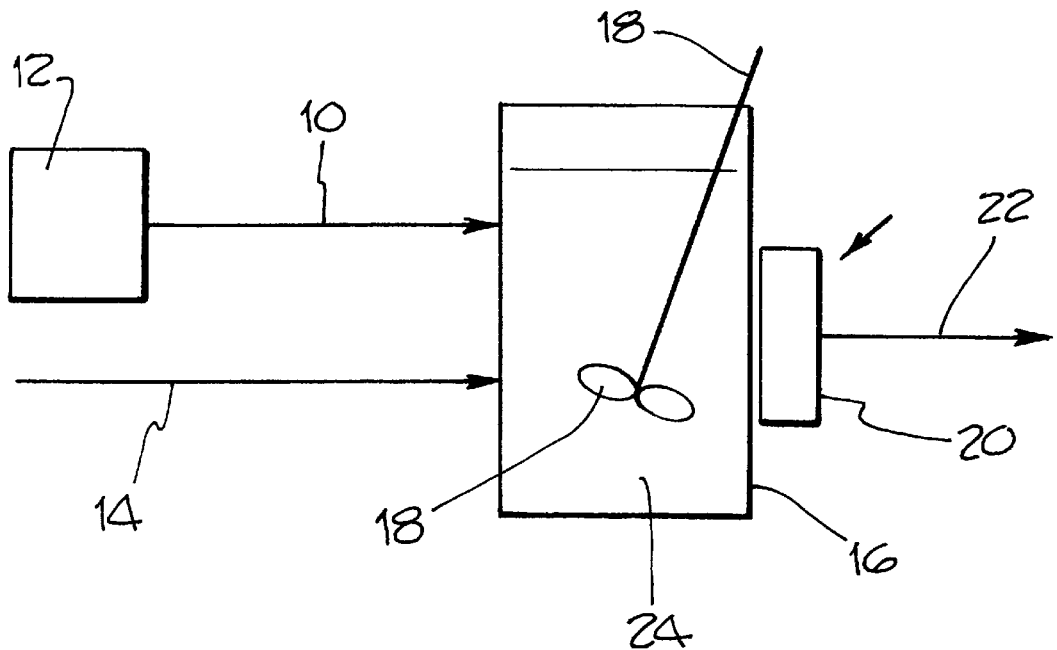
FIG. 16 depicts a continuous metal ion concentration monitoring system based on the invention. A continuous sample stream is mixed with a stream containing the mixed liposomes coming from a reservoir. The fluorescence intensity is measured continuously directly in the mixing cell or on the outlet stream. For a quantitative determination of metal ion concentration, this continuous signal can be compared to a reference signal obtained from a sample stream of known metal concentration or from a single reference sample.

The lipid-based metal sensor of the present invention can also be used to continuously monitor metal ion concentrations in a sample stream. As indicated schematically in FIG. 16, this can be done by continuously mixing a stream 10 containing the mixed liposomes from a reservoir 12 with the sample stream 14 in a cell 16 using a mixing device 18. A fluorescence detector 20 is used to monitor the fluorescence intensity of either the outlet stream 22 or the contents of the cell 24. The cell 16 can be, for example, a cuvette for a fluorescence spectrometer with provision for sample mixing, such as a magnetic stirring device. Alternatively, the outlet stream 22 can be directed to a fluorescence spectrometer. As shown in FIG. 16, as the sample stream 14 enters the cell 16, it becomes mixed with the liposome-containing stream 10 coming from the reservoir 12. If the cell 16 is well-mixed, the metal ion concentration, and therefore fluorescence intensity of the outlet stream 22 will be the same as the contents 24 of the cell 16. A change in the concentration of metal ions in the sample stream 14 over time will be reflected in a change in the fluorescence intensity of the liposome sample mixture 24. Metal ion concentrations can be determined by comparison to the single signal from a reference sample of known metal concentration or from the continuous signal from a duplicate cell in which a reference stream is added to the liposomes.

Figure 17:
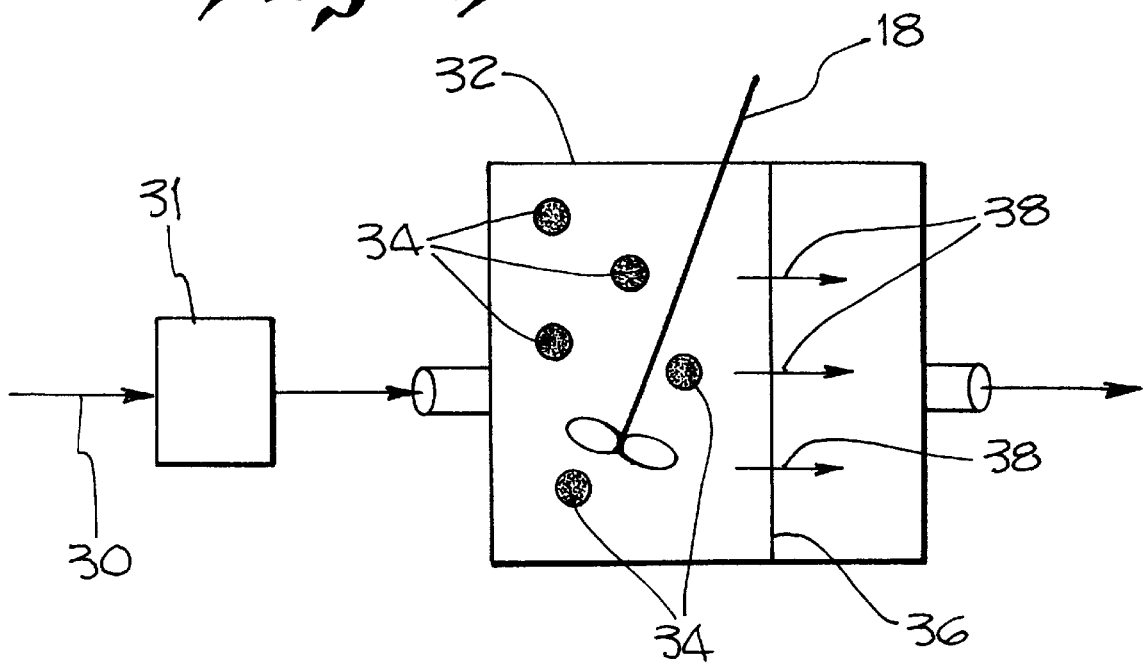
FIG. 17 depicts a second exemplary method by which the present invention can be used to continuously measure metal ion concentrations in a sample stream.

FIG. 17 depicts a second exemplary method by which the present invention can be used to continuously measure metal ion concentrations in a sample stream. The sample stream 30 containing the metal ions (appropriately pre-filtered in filter 31 to remove particulates and large molecules) is pumped into a cell containing the mixed liposomes 34 (with the fluorescent metal-chelating amphiphile) and an ultrafiltration membrane 36. The membrane 36 retains the large liposomes 34, while allowing water, metal ions and other small molecules to pass through as indicated by arrows 38. The fluorescence emission of the liposomes is measured continuously in the sample cell 32. As in previous embodiments, the relative emission intensities at the monomer and excimer wavelengths are related to the concentration of metal ion in the sample cell.

The ability of this configuration to follow a time-varying metal ion concentration depends on the rate at which the metal-chelating liposomes can respond to changes in metal concentration in the sample cell 32. This response is related to the rate at which the metal ions are released by the liposomes 34. When the rate of equilibration is fast, this system can respond to rapidly-changing metal concentrations. When slow, the system can detect only slowly-changing concentrations. These metal release rates can be controlled to some extent by optimizing the chelating head group of the fluorescent metal-chelating amphiphile and the conditions of the sample cell (temperature, pH, etc.).

Examples of practice are as follows:

EXAMPLE 1

Synthesis of pyrene stearyl iminodiacetic acid (PSIDA)

Figure 2:
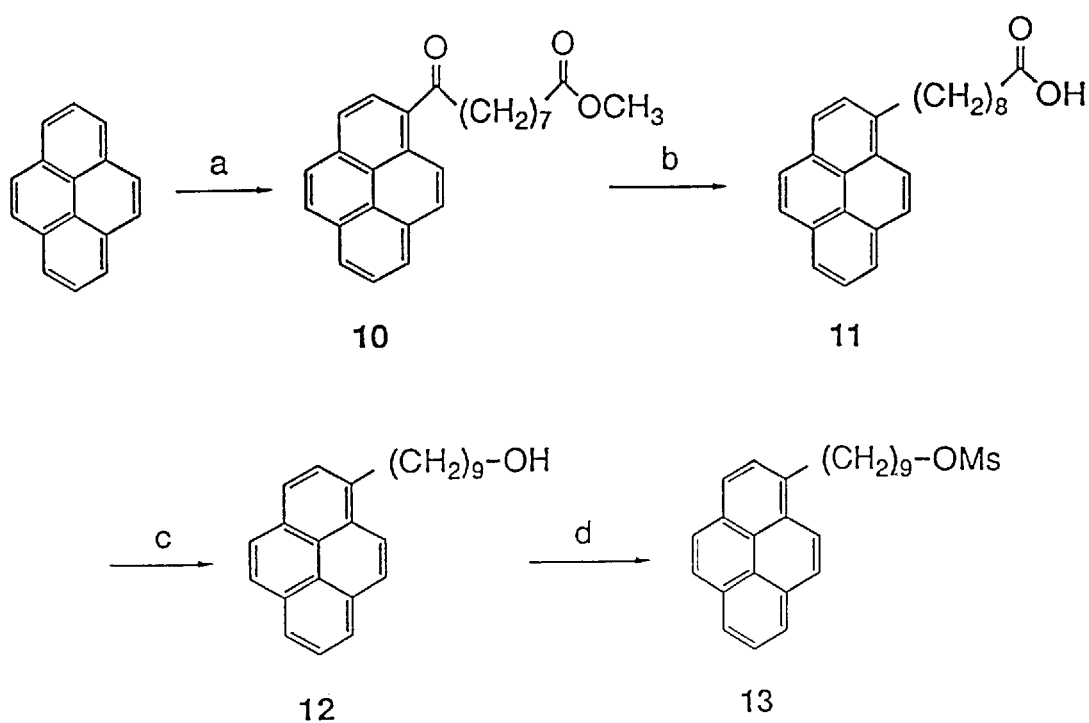
FIG. 2 is a diagram of the synthesis scheme for making one of the intermediate compounds required in the synthetic pathway set forth in FIG. 1.

The metal-chelating fluorescent lipid pyrene stearyl iminodiacetic acid (PSIDA) was synthesized in accordance with the present invention according to the multistep sequence outlined in FIG. 1. The following bold numerical references correspond to the numbered compounds shown in FIGS. 1 and 2. PSIDA (9) has a glycerol hydrophilic backbone connecting two alkyl tails at the 2 and 3 positions. The iminodiacetic acid headgroup is connected to the backbone on the 1 position by a hydrophilic spacer. The alkyl tails are connected to the glycerol backbone through ether linkages. The synthesis required several protection-deprotection steps to generate the asymmetrical fluorescent lipid 9. The octadecyl alkyl chain was first attached to the acetonide-protected glycerol in good yield. Deprotection of the acetonide with acid and subsequent selective protection at the 1 position gave 3. A pyrene-tagged nonyl alcohol 12 was prepared by a modified procedure from de Bony, J.; Tocanne, J.-F., *Chem. Phys. Lipids* (1983), 32, 105 and Sunamoto, J., Kondo, H., Nomura, T., Okamoto, H., *J. Am. Chem. Soc.* (1980), 102, 1146, as shown in FIG. 2. The alcohol was activated as the mesylate 13 which was then appended to the glycerol at the 2 position to give 4. Deprotection of the trityl group was followed by etherification with 15 (FIG. 3) to introduce the triethylene glycol spacer group to the main lipid body 5. Subsequent functional group manipulation gave the iminodiacetic acid headgroup and lipid PSIDA 9.

Details of the synthesis of PSIDA 9 are as follows:

All reactions were performed in oven-dried (160° C.) glassware under positive $N_2$ atmosphere. Tetrahydrofuran (THF) was distilled from Na-benzophenone, and DMSO was dried over 3 Å molecular sieves. Methanesulfonylchloride, triethylamine ($NEt_3$), solketal, and diethyliminodiacetate (Kodak) were dried and distilled prior to use. All other reagents were used as received. Preparation of compounds 10 and 11 are modifications of procedures from de Bony, J.; Tocanne, J.-F., *Chem. Phys. Lipids* (1983), 32, 105. All $^1H$ and $^{13}C$ NMR were performed in $CDCl_3$ on a Nicolet QE-300 NMR spectrometer, and infrared (IR) spectra were obtained on a Perkin-Elmer 1600 Series FTIR spectrometer. Chemical analyses were performed by Desert Analytics (Tucson, Ariz.). All flash column chromatography was performed with Merck grade 60 silica gel. Melting point determinations were done on a Laboratory Devices Mel-Temp II and are uncorrected.

Preparation of octadecyl solketal ether (1)—step "a" in FIG. 1. Solketal (5.00 g, 37.8 mmole) was dissolved in DMSO (100 mL) along with KOH (6.4 g, 0.11 mole) and stirred for 15 minutes. 1-Methanesulfonyl octadecane (10.0 g, 28.7 mmole) was added as a solid, and the solution was stirred for 14 hours at 70° C. The solution was then cooled to room temperature and diluted with $Et_2O$ (100 mL) and $H_2O$ (200 mL). The mixture was shaken, layers separated, and the aqueous layer extracted with fresh $Et_2O$ (2×100 mL). The organics were combined and washed with $H_2O$ (2×100 mL), followed by aq. sat. NaCl (100 mL). It was then dried over anhydrous $MgSO_4$, filtered, solvent stripped in vacuo, and the residual oil was flash column chromatographed with $Et_2O$/hexanes (10% v/v, $R_f$=0.32). Product 1 was recovered as a clear, colorless oil that crystallized upon standing at room temperature (9.95 g, 97%: mp 32°–34° C.). $^1H$ NMR δ4.26 (m, 1H, OCH), 4.06 (dd, J=8.1, 6.5 Hz, 1H, $OC(H_a)H_e$), 3.73 (dd, J=8.0, 6.6 Hz, 1H, $OCH_a(H_e)$), 3.54–3.39 (m, 4H, $OCH_2$), 1.57 (m, 2H, $OCH_2CH_2$), 1.42 (s, 3H, OC—$CH_3$), 1.36 (s, 3H, OC—$CH_3$), 1.25–1.16 (m, 30H), 0.88 (t, J=6.5 Hz, 3H, —$CH_3$). $^{13}C$ NMR δ109.33, 74.74, 71.89, 71.81, 66.93, 31.93, 29.70, 29.61, 29.47, 29.37, 26.77, 26.06, 25.42, 22.70, 14.13. IR (neat) 2924, 2853, 1466, 1379, 1369, 1255, 1214, 1118, 1056, 846 cm$^{-1}$.

Preparation of 1-octadecylglycerol (2)—step "b" in FIG. 1. Compound 1 (6.00 g, 16.8 mmole) was placed in a mixture of MeOH (70 mL) and 1N HCl (4 mL) and stirred at 60° C. for 3 hours. The solution was allowed to cool to room temperature, and product 2 slowly crystallized out of solution. The crystals-were collected and recrystallized twice in MeOH (5.10 g, 88%: mp 70°–71° C.). $^1H$ NMR δ3.86 (m, 1H, CH(OH)), 3.68 (m, 2H, $CH_2(OH)$), 3.50 (m, 4H, $CH_2OCH_2$), 2.66 (d, J=4.9 Hz, 1H, CH(OH)), 2.24 (t, J=5.7 Hz, 1H, $CH_2(OH)$), 1.56 (m, 2H, $CH_2CH_2O$), 1.27 (m, 30H), 0.88 (t, J=6.6 Hz, 3H, —$CH_3$). $^{13}C$ NMR δ72.83, 72.49, 72.17, 71.83, 64.28, 31.93, 29.69, 26.07, 22.70, 14.21. IR (KBr) 3356, 2919, 2850, 1472, 1374, 1122, 1061, 937, 683 cm$^{-1}$.

Preparation of 1-octadecyl-3-triphenylcarbinylglycerol(3) —step "c" in FIG. 1. Tritylchloride (3.24 g, 11.6 mmole), DMAP (70 mg, 0.57 mmole) and 2 (4.00 g, 11.6 mmole) were placed in $CH_2Cl_2$ (50 ml) and stirred. To the solution was added triethylamine (5.0 mL, 36 mmole), and the reaction proceeded for 12 hours at room temperature. The solution was then diluted with $CH_2Cl_2$ (30 mL) and $H_2O$ (70 mL), the mixture shaken, and layers separated. The aqueous layer was extracted with fresh $CH_2Cl_2$ (2×70 mL), the organics combined and washed with $H_2O$ (2×100 mL), then once with aq. sat. NaCl (70 mL). The organics were further dried over $MgSO_4$, filtered, concentrated in vacuo, then flash column chromatographed with $CH_2Cl_2$/hexanes (75 % v/v, $R_f$=0.17). Product 3 was collected as white crystals (5.40 g, 79%: mp 56°–57° C.). $^1H$ NMR δ7.45 (m, 6H, Ar-H), 7.27

(m, 9H, Ar-H), 3.96 (m, 1H, CH(OH)), 3.56–3.40 (m, 4H, CH$_2$OCH$_2$), 3.20 (m, 2H, CH$_2$OCPh$_3$), 2.42 (d, J=4.6 Hz, 1H, —OH), 1.54 (m, 2H, CH$_2$CH$_2$O), 1.27 (m, 30H), 0.88 (t, J=6.6 Hz, 3H, —CH$_3$). $^{13}$C NMR δ143.84, 128.64, 127.82, 127.08, 86.58, 72.00, 71.63, 70.11, 69.53, 64.56, 31.93, 29.70, 29.52, 26.10, 22.71, 14.26. IR (KBr) 3448, 3056, 2918, 2850, 1491, 1470, 1446, 1210, 1077, 757, 702, 634 cm$^{-1}$.

Preparation of 3-octadecyloxy-2-(9-(1-pyrene)nonyloxy)-1-triphenylcarbinyloxypropane (4)—step "d" in FIG. 1. Compound 3 (2.78 g, 4.74 mmole) and KOH (0.80 g, 14.3 mmole) were placed in DMSO (50 mL) and stirred at 80° C. for 20 minutes. Compound 13 (2.00 g, 4.74 mmole) was then added as a solid and the reaction was allowed to proceed for 12 hours. The procedure for making 13 is outlined in FIG. 2 and described in detail below. The solution was then cooled to room temperature and diluted with Et$_2$O (100 mL) and H$_2$O(150 mL), the mixture shaken, layers separated, and the aqueous layer extracted with fresh Et$_2$O (2×70 mL). The organics were combined and washed with H$_2$O (2×100 mL) then once with aq. sat. NaCl (50 mL), followed by drying over anhydrous MgSO$_4$, filtered, and concentrated in vacuo. The residuals were flash column chromatographed with CH$_2$Cl$_2$/hexanes (50% v/v, R$_f$=0.30). Product 4 was obtained as a yellow oil (2.25 g, 52%). $^1$H NMR δ8.28 (d, J=9.3 Hz, 1H, Py—H), 8.16–7.95 (m, 7H, Py—H), 7.86 (d, J=7.8 Hz, 1H, Py—H), 7.46 (m, 6H, Py—H), 7.30–7.18 (m, 9H, Py—H), 3.55–3.49 (m, 5H, C(H)O), 3.38 (t, J=6.6 Hz, 2H, CH$_2$O), 3.32 (t, J=7.8 Hz, 2H, Py—CH$_2$), 3.16 (m, 2H, CH$_2$OCPh$_3$), 1.84 (m, 2H, Py—CH$_2$CH$_2$), 1.58–1.24 (m, 44H), 0.87 (t, J=6.5 Hz, 3H, —CH$_3$). $^{13}$C NMR δ144.13, 137.33, 130.92, 129.64, 128.73, 127.92, 127.70, 127.53, 127.24, 127.06, 126.87, 126.45, 125.73, 125.05, 124.75, 124.59, 123.53, 86.58, 78.28, 71.61, 71.15, 70.68, 63.55, 33.64, 31.97, 30.12, 29.85, 29.72, 29.56, 29.39, 26.15, 26.11, 22.71, 14.17. IR (neat) 3037, 2924, 2852, 1686, 1490, 1448, 1117, 843, 705 cm$^{-1}$. Anal. Calcd for C$_{65}$H$_{84}$O$_3$: C, 85.48; H, 9.27. Found: C, 85.88; H, 9.23.

Preparation of 3-Octadecyloxy-2-(9-(1-pyrene)nonyloxy)propan-1-ol (5)—step "e" in FIG. 1. Into a mixture of THF (20 mL)/MeOH (20 mL) was dissolved 4 (2.20 g, 2.41 mmole) and TsOH.H$_2$O (70 mg, 0.37 mmole). The solution was stirred for 13 hours at which time triethylamine (0.10 mL) was added prior to solution concentration in vacuo. Flash column chromatography was performed with Et$_2$O/CH$_2$Cl$_2$ (2% v/v, R$_f$=0.18). Yellow crystalline 5 was recovered (1.51 g, 93%: mp 35°–36° C.). $^1$H NMR δ8.27 (d, J=9.3 Hz, 1H, Py—H), 8.16–7.95 (m, 7H, Py—H), 7.86 (d, J=7.8 Hz, 1H Py—H), 3.70 (br s, 1H, CH—O), 3.63–3.39 (m, 8H, CH$_2$—O), 3.32 (t, J=7.7 Hz, 2H, Py—CH$_2$), 2.19 (br s, 1H, —OH), 1.84 (m, 2H, Py—CH$_2$CH$_2$), 1.56–1.24 (m, 44H), 0.87 (t, J=6.4 Hz, 3H, —CH$_3$). $^{13}$C NMR δ137.29, 131.41, 130.90, 128.56, 127.52, 127.23, 127.06, 126.45, 125.73, 124.75, 124.58, 123.50, 78.17, 71.84, 70.88, 70.35, 63.10, 33.63, 31.95, 30.04, 29.71, 29.62, 29.48, 29.39, 26.09, 22.71, 14.16. IR (KBr) 3444, 3037, 2917, 2850, 1468, 1118, 840 cm$^{-1}$. Anal. Calcd for C$_{46}$H$_{70}$O$_3$: C, 82.33; H, 10.51. Found: C, 82.58; H, 10.25.

Preparation of 3-octadecyloxy-2-(9-(1-pyrene)nonyloxy)-propan-1-(9(3,6,9-trioxynonan-1-ol)) (6)—step "f" in FIG. 1. Compound 5 (1.40 g, 2.09 mmole) in THF (20 mL) was syringed into a suspension of NaH (0.33 g of a 60% oil dispersion, 8.3 mmole) in THF (20 mL) and the mixture stirred for 30 minutes at room temperature. Compound 15 (1.28 g, 2.72 mmole) was then added as a solid and the reaction brought to reflux for 10 hours. The procedure for making 15 is outlined in FIG. 3 and described in detail below. The solution was then cooled to room temperature, diluted with Et$_2$O (80 mL) and H$_2$O (100 mL), the mixture shaken, layers separated, and the aqueous layer extracted with fresh Et$_2$O (2×70 mL). The organics were combined and washed once with H$_2$O (100 mL) followed by aq. sat. NaCl (70 mL). The organics were dried over anhydrous MgSO$_4$, filtered and concentrated in vacuo. The oils were then taken up in THF (10 mL)/MeOH (10 mL) solution along with TsOH.H$_2$O (70 mg) and the mixture stirred for 5 hours. Triethylamine (0.10 mL) was then added and the solution was concentrated in vacuo and flash column chromatographed with EtOAc/hexanes (40% v/v, R$_f$=0.13). Product 6 was obtained as a yellow oil (1.47 g, 88%). $^1$H NMR δ8.27 (d, J=9.3 Hz, 1H, Py—H), 8.16–7.97 (m, 7H, Py—H), 7.85 (d, J=7.8 Hz, 1H, Py—H), 3.72–3.39 (m, 21H, C(H)—O), 3.32 (t, J=7.8 Hz, 2H, Py—CH$_2$), 2.64 (br s, 1H, —OH), 1.84 (m, 2H, Py—CH$_2$CH$_2$), 1.54–1.24 (m, 44H), 0.87 (t, J=6.6 Hz, 3H, —CH$_3$). $^{13}$C NMR δ137.29, 131.40, 130.89, 129.63, 127.50, 127.20, 127.04, 126.42, 125.70, 125.02, 124.73, 124.57, 123.49, 77.82, 72.51, 71.64, 71.35, 70.78, 70.61, 70.55, 70.32, 61.72, 33.62, 31.95, 31.93, 30.04, 29.82, 29.70, 29.66, 29.56, 29.50, 29.37, 26.11, 26.06, 22.70, 14.14. IR (neat) 3448, 3040, 2922, 2852, 1466, 1350, 1134, 844 cm$^{-1}$. Anal. Calcd for C$_{52}$H$_{82}$O$_6$: C, 77.76; H, 10.29. Found: C, 77.87; H, 10.42.

Preparation of 3-octadecyloxy-2-(9-(1-pyrene) nonyloxy)-propan-1-(9(1-bromo-3,6,9-trioxynonane)) (7)—step "g" in FIG. 1. Compound 6 (0.60 g, 0.75 mmole) was dissolved in THF (10 mL) and the solution cooled to 5° C. Carbon tetrabromide (0.37 g, 1.1 mmole) and triphenylphosphine (0.29 g, 1.1 mmole) were added to the solution, which was stirred for 12 hours. The solution was then concentrated in vacuo and flash column chromatographed with Et$_2$O/hexanes (40% v/v, R$_f$=0.26). Product 7 was obtained as a yellow oil (0.61 g, 94%). $^1$H NMR δ8.28 (d, J=9.3 Hz, 1H, Py—H), 8.17–7.98 (m, 7H, Py—H), 7.86 (d, J=7.8 Hz, 1H, Py—H), 3.78 (t, J=6.2 Hz, 2H, CH$_2$Br), 3.64–3.40 (m, 19H, C(H)—O), 3.33 (t, J=7.8 Hz, 2H, Py—CH$_2$), 1.85 (m, 2H, Py—CH$_2$CH$_2$), 1.54–1.24 (m, 44H), 0.87 (t, J=6.6 Hz, 3H, —CH$_3$). $^{13}$C NMR δ137.31, 131.42, 130.91, 129.66, 127.52, 127.23, 127.06, 126.45, 125.73, 124.75, 124.59, 123.52, 77.82, 71.66, 71.39, 71.19, 70.86, 70.70, 70.59, 33.64, 31.98, 31.94, 30.30, 30.08, 29.84, 29.71, 29.67, 29.57, 29.52, 29.38, 26.13, 26.08, 22.70, 14.16. IR (neat) 3037, 2923, 2852, 1465, 1350, 1134, 844 cm$^{-1}$. Anal. Calcd for C$_{52}$H$_{81}$O$_5$Br: C, 72.11; H, 9.43.

Found: C, 72.04; H, 9.27.

Preparation of 3-octadecyloxy-2-(9-(1-pyrene)nonyloxy)-propan-1-(9-(3,6,9-trioxynonyl-1-amino-N,N-diethyldiacetate)) (8)—step "h" in FIG. 1. Compound 7 (0.60 g, 0.69 mmole), diethyliminodiacetate (0.52 g, 2.7 mmole), and triethylamine (0.40 mL, 2.9 mmole) were placed in CH$_3$CN (10 mL)/THF (4 mL) solution and refluxed for three days. The reaction mixture was cooled to room temperature, concentrated in vacuo, and flash column chromatographed with EtOAc/hexanes (40% v/v, R$_f$=0.26). A yellow oil was obtained and identified as 8 (0.26 g, 39%). $^1$H NMR δ8.27 (d, J=9.3 Hz, 1H, Py—H), 8.1 6–7.97 (m, 7H, Py—H), 7.86 (d, J=7.8 Hz, 1H, Py—H), 4.15 (q, J=7.1 Hz, 4H, (C=O)OCH$_2$CH$_3$), 3.61–3.39 (m, 23H, C(H)—O, N—CH$_2$(C=O)), 3.32 (t, J=7.8 Hz, 2H, Py—CH$_2$), 2.96 (t, J=5.6 Hz, 2H, CH$_2$CH$_2$—N), 1.84 (m, 2H, Py—CH$_2$CH$_2$), 1.54–1.24 (m, 50H, aliphatic —CH$_2$ (C=O)CH$_2$CH$_3$), 0.87 (t, J=6.6 Hz, 3H, —CH$_3$). $^{13}$C NMR δ171.37, 137.29, 131.39, 130.89, 129.61, 127.50, 127.20, 127.04, 126.42, 125.70, 125.02, 124.72, 124.56, 123.49, 77.80, 71.62, 71.35, 70.80, 70.75, 70.51, 70.32, 60.42, 55.87, 53.55, 33.62, 31.95, 30.06, 29.83, 29.69, 29.54, 29.50, 29.36, 26.10, 22.69, 14.24, 14.14. IR (neat) 3040, 2924, 2853, 1745, 1466, 1186, 1116, 1032, 844 cm$^{-1}$. Anal. Calcd for $C_{60}H_{95}NO_9$: C, 73.96, H, 9.83; N, 1.44. Found: C, 73.58; H, 9.67; N, 1.55.

Preparation of 3-octadecyloxy-2-(9-(1-pyrene)nonyloxy)-propan-1-(9(3,6,9-trioxynonyl-1-amino-N,N-diacetic acid)) (9) or PSIDA—step "i"n in FIG. 1. Into a solution of THF (6 mL)/MeOH (6 mL)/H$_2$O (1 mL) were placed 8 (200 mg, 0.206 mmole) and crushed NaOH (50 mg). The homogeneous mixture was refluxed for 1 h, cooled to room temperature, and then acidified to pH 1. The solution was solvent stripped in vacuo, then taken up in Et$_2$O (30 mL) and aq. sat. NaCl (20 mL). The mixture was shaken, layers separated, and the aqueous emulsion was extracted with fresh Et$_2$O (2×30 mL). The final extraction removed the emulsion and two cleanly separated phases were observed. The organics were combined and dried over anhydrous MgSO$_4$, filtered, and solvent removed. The waxy material was then taken up in CH$_2$Cl$_2$ and run through a small plug of silica gel. Removal of solvent in vacuo yielded product 9 as a yellow waxy material (160 mg, 85%). $^1$H NMR δ10.18 (br s, 2H, —COOH), 8.25 (d, J=9.3 Hz, 1H, Py—H), 8.14–7.96 (m, 7H, Py—H), 7.84 (d, J=7.8 Hz, 1H, Py—H), 4.01 (br s, 4H, N—CH$_2$—CO$_2$H), 3.75 (br s, 2H, CH$_2$CH$_2$—N), 3.60–3.38 (m, 19H, O—C(H)), 3.30 (t, J=7.7 Hz, 2H, Py—CH$_2$), 1.82 (m, 2H, Py—CH$_2$CH$_2$), 1.52–1.22 (m, 44H), 0.86 (t, J=6.5 Hz, 3H, —CH$_3$). $^{13}$C NMR δ169.56, 137.30, 130.88, 129.61, 128.53, 127.51, 127.21, 127.06, 126.43, 125.72, 125.02, 124.74, 124.58, 123.50, 77.76, 71.72, 71.23, 70.95, 70.53, 70.38, 70.23, 56.86, 56.78, 33.62, 31.96, 30.00, 29.83, 29.72, 29.55, 29.38, 26.09, 26.06, 22.70, 14.16. IR (neat) 3044, 2923, 2852, 1734, 1466, 1244, 1115, 843, 720 cm$^{-1}$. Anal. Calcd for $C_{56}H_{89}NO_{10}$: C, 71.84; H, 9.58; N, 1.50. Found: C, 71.53; H, 9.13; N, 1.57.

The preparation of 9-(1-pyrene)-1-methane sulfonyl-nonane (13) was carried out as follows:

Preparation of 9-(1-pyrene)-9-oxomethylnonanoate (10)—step "a" in FIG. 2. Pyrene (7.51 g, 37.1 mmole) was dissolved in nitrobenzene (100 mL) and cooled to 10° C. To the stirred mixture was added AlCl$_3$ (6.93 g, 52.0 mmole) portionwise through a solid addition funnel. Monomethylazelaic acid chloride (5.45 g, 24.8 mmole; prepared as in reference Hickinbottom, "Reaction of Organic Compounds", Longmans, London, 1957; de Bony, J.; Tocanne, J.-F., *Chem. Phys. Lipids* (1983), 32, 105) in nitrobenzene (10 mL) was then added to the mixture dropwise via an addition funnel. The mixture was then allowed to come to room temperature slowly, and the reaction was allowed to proceed for 2 days. The reaction mixture was then poured over ice and the mixture stirred for a few hours. The solution was placed in a separatory funnel along with CH$_2$Cl$_2$ (100 mL), shaken, layers separated, and the aqueous layer was extracted with fresh CH$_2$Cl$_2$ (2×100 mL). The organics were combined and washed with H$_2$O (100 mL), followed by aq. sat. NaHCO$_3$ (100 mL), and aq. sat. NaCl (100 mL). The organics were dried over anhydrous MgSO$_4$, filtered, stripped of low boiling solvents on a rotovap, and most of the nitrobenzene was removed by distillation at 60° C., 4 mmHg. The residual material in the pot was recrystallized in 9:1 EtOH/benzene (150 mL) and the crystals collected and flash column chromatographed with Et$_2$O/benzene (2% v/v, R$_f$=0.17). Product 10 was recrystallized twice in EtOH/benzene to yield light yellow crystal flakes (6.86 g, 72%: mp 83°–85.5° C.). $^1$H NMR δ8.86 (d, J=9.4 Hz, 1H, Py—H), 8.31–8.02 (m, 8H, Py—H), 3.66 (s, 3H, CO$_2$CH$_3$), 3.20 (t, J=7.4 Hz, 2H, Py—(C═O)CH$_2$), 2.30 (t, J=7.5 Hz, 2H, CH$_2$CO$_2$), 1.85 (m, 2H, Py—(C═O)CH$_2$CH$_2$), 1.62 (m, 2H, CH$_2$CH$_2$CO$_2$), 1.46–1.34 (m, 6H). $^{13}$C NMR δ205.32, 174.26, 133.56, 132.87, 131.08, 130.55, 129.47, 129.38, 129.22, 127.08, 126.36, 126.17, 125.96, 124.78, 124.35, 124.01, 51.47, 42.61, 34.05; 29.21, 29.14, 28.99, 24.88. IR (KBr) 3067, 2926, 2855, 1736, 1670, 1593, 1466, 1247, 1207, 1169, 852 cm$^{-1}$.

Preparation of 9-(1-pyrene)nonanoic acid (11)—step "b" in FIG. 2. Compound 10 (4.26 g, 11.0 mmole), NaOH (2.21 g, 55.3 mmole) and H$_2$NNH$_2$.H$_2$O (1.34 mL, 27.6 mmole) were placed in triethyleneglycol (50 mL) and the mixture warmed to 120° C. for 1 hour, followed by heating to 195°–200° C. for 2 hours. The mixture was then cooled to room temperature and diluted with CH$_2$Cl$_2$ (70 mL) and H$_2$O (100 mL). The aqueous layer was acidified to pH 1–2 with 1N HCl, the mixture shaken and the layers separated. The aqueous layer was extracted with fresh CH$_2$Cl$_2$ (3×70 mL), the organics combined and washed with H$_2$O (2×70 mL) then once with aq. sat. NaCl (70 mL). The organics were dried over anhydrous MgSO$_4$, filtered, and solvent removed under vacuo. The solids were recrystallized in EtOH (120 mL) and yellow crystals of 11 were collected (3.20 g, 81%: mp 123°–124° C.). $^1$H NMR δ11.33 (br s, 1H, —CO$_2$H), 8.26 (d, J=9.3 Hz, 1H, Py—H), 8.05 (m, 7H, Py—H), 7.84 (d, J=7.8 Hz, 1H, Py—H), 3.31 (t, J=7.8 Hz, 2H, Py—CH$_2$), 2.33 (t, J=7.4 Hz, 2H, CH$_2$CO$_2$H), 1.83 (m, 2H, Py—CH$_2$CH$_2$), 1.62 (m, 2H, CH$_2$CH$_2$CO$_2$H), 1.41 (m, 8H). $^{13}$C NMR δ179.82, 137.24, 131.43, 130.92, 129.67, 128.57, 127.52, 127.23, 127.08, 126.46, 125.74, 125.05, 124.76, 124.60, 123.50, 33.97, 33.59, 31.90, 29.72, 29.35, 29.20, 29.02, 24.64. IR (KBr) 3036, 2925, 2856, 1702, 1468, 1406, 1248, 960, 841, 710 cm$^{-1}$.

Preparation of 9-(1-pyrene)nonan-1-ol (12)—step "c" in FIG. 2. Compound 11 (2.39 g, 6.68 mmole) in THF (20 mL) was added to a solution of LiAlH$_4$ (10.0 mL of a 1.0M solution in THF, 10.0 mmole) in THF (30 mL). The mixture was refluxed for 1 hour, then cooled to 0° C. and quenched with H$_2$O (0.38 mL), followed by 10% NaOH (0.38 mL) and then H$_2$O (1.14 mL). The mixture was stirred for 10 minutes. Anhydrous MgSO$_4$ was added, the reaction filtered and solvent removed in vacuo. Product 12 was obtained as a yellow powder (2.07 g, 90%: mp 73.5°–75.5° C.). $^1$H NMR δ8.23 (d, J=9.3 Hz, 1H, Py—H), 8.12–7.91 (m, 7H, Py—H), 7.81 (d, J=7.8 Hz, 1H, Py—H), 3.56 (t, J=6.6 Hz, 2H, —CH$_2$OH), 3.28 (t, J=7.7 Hz, 2H, Py—CH$_2$), 1.80 (m, 2H, Py—CH$_2$CH$_2$), 1.49–1.26 (m, 13H). $^{13}$C NMR δ137.24, 131.37, 130.86, 129.60, 128.52, 127.48, 127.18, 127.02, 126.41, 125.69, 125.19, 124.99, 124.71, 124.55, 123.46, 62.98, 33.57, 32.71, 31.89, 29.75, 29.51, 29.38, 25.67. IR (KBr) 3315, 3036, 2926, 2855, 1468, 1438, 1364, 1183, 1054, 840, 709 cm$^{-1}$.

Preparation of 9-(1-pyrene)-1-methanesulfonyl nonane (13)—step "d" in FIG. 2. Into dry THF (50 mL) were placed 12 (2.07 g, 6.02 mmole) and triethylamine (2.05 mL, 14.7 mmole) and the stirred mixture was cooled to 0° C. Methanesulfonyl chloride (0.78 mL, 10.0 mmole) was then added by syringe and the reaction allowed to proceed for 2.5 hours. The reaction was then diluted with Et$_2$O (70 mL) and H$_2$O (70 mL), the mixture shaken, layers separated, and the aqueous layer extracted with fresh Et$_2$O (2×70 mL). The organics were combined and washed with cold 1N HCl (70 mL), followed by cold aq. sat. NaHCO$_3$ (70 mL) and finally aq. sat. NaCl (70 mL). The organics were then dried over anhydrous MgSO$_4$, filtered, and evaporated to dryness. The yellow powder of 13 was obtained (2.39 g, 94%: mp 77.5°–80° C.). $^1$H NMR δ8.27 (d, J=9.3 Hz, 1H, Py—H), 8.17–7.95 (m, 7H, Py—H), 7.86 (d, J=7.8 Hz, 1H, Py—H), 4.19 (t, J=6.6 Hz, 2H, CH$_2$O), 3.33 (t, J=7.7 Hz, 2H, Py—CH$_2$), 2.97 (s, 3H, SO$_2$CH$_3$), 1.84 (m, 2H, Py—CH$_2$CH$_2$), 1.71 (m, 2H, OCH$_2$CH$_2$), 1.49–1.32 (m, 10H). $^{13}$C NMR δ137.23, 131.41, 129.65, 127.52, 127.25, 127.08, 126.47, 125.76, 125.03, 124.76, 124.60, 123.49, 70.18, 37.32, 33.60, 31.91, 29.71, 29.44, 29.37, 29.07, 29.00, 28.89, 25.39. IR (KBr) 3032, 2926, 2856, 1602, 1469, 1340, 1174, 986, 952, 915, 841, 710 cm$^{-1}$.

Figure 3:
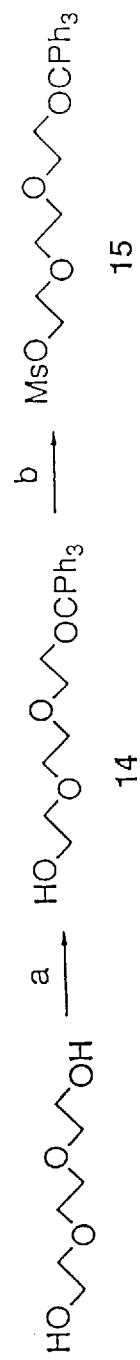
FIG. 3 is a diagram of the synthesis scheme for making another one of the intermediate compounds required in the synthetic pathway set forth in FIG. 1.

The preparation of 1-methanesulfonyl-9-triphenylcarbinyl-3, 6,9-trioxynonane (15) was carried out as shown in FIG. 3. Details of the synthesis are as follows:

Preparation of 9-triphenylcarbinyl-3,6,9-trioxynona-1-ol (14)—step "a" in FIG. 3. Triethylene glycol (10.0 g, 66.6 mmole), tritylchloride (14.8 g, 53.1 mmole), and DMAP (320 mg, 2.62 mmole) were dissolved in CH$_2$Cl$_2$ (100 mL). To the stirred solution was added triethylamine (18.0 mL, 129 mmole) by syringe followed by stirring for 12 hours. The solution was then diluted with CH$_2$Cl$_2$ (70 mL) and H$_2$O (100 mL), the mixture shaken, layers separated and the aqueous layer extracted with fresh CH$_2$Cl$_2$ (2×70 mL). The organics were combined and washed with H$_2$O (100 mL), followed by 1N HCl (100 mL), aq. sat. NaHCO$_3$ (100 mL), and then aq. sat. NaCl (70 mL). The organics were further dried over anhydrous MgSO$_4$, filtered and concentrated in vacuo followed by flash column chromatography with EtOAc/hexanes (50% v/v; R$_f$=0.18). Compound 14 was obtained as a viscous oil (11.5 g, 44%).

Preparation of 1-methanesulfonyl-9-triphenylcarbinyl-3, 6,9-trioxynonane (15)—step "b" in FIG. 3. 14 (11.5 g, 29.3 mmole) and triethylamine (6.1 mL, 44 mmole) were placed in CH$_2$Cl$_2$ (60 mL) and stirred at 0° C. for 15 minutes. Methanesulfonylchloride (2.7 mL, 35 mmole) was then added dropwise to the solution and the reaction stirred for 5 hours. The reaction was quenched with H$_2$O (50 mL) and then diluted with CH$_2$Cl$_2$ (30 mL). The mixture was shaken, layers separated and the aqueous layer extracted with fresh CH$_2$Cl$_2$ (2×40 mL). The organics were combined and washed with 1N HCl (40 mL), followed by aq. sat. NaHCO$_3$ (40 mL), and aq. sat. NaCl (40 mL). The organics were further dried over anhydrous MgSO$_4$, filtered, and concentrated in vacuo. The residual oil was taken up in 1:2 benzene/hexanes (30 mL) and allowed to crystallize. Product 15 was collected as white crystals (13.2 g, 96%: mp 89°–90.5° C.). $^1$H NMR δ7.45 (d, J=7.2 Hz, 6H, Ph—H), 7.32–7.20 (m, 9H, Py—H), 4.36 (t, J=4.4 Hz, 2H, CH$_2$OSO$_2$—), 3.78 (t, J=4.4 Hz, 2H, CH$_2$CH$_2$OSO$_2$—), 3.69 (s, 4H, —OCH$_2$CH$_2$O—), 3.66 (t, J=5.1 Hz, 2H, CH$_2$CH$_2$OCPh$_3$), 3.23 (t, J=5.1 Hz, 2H, CH$_2$OCPh$_3$), 2.95 (s, 3H, SO$_2$CH$_3$). $^{13}$C NMR δ161.41, 144.00, 128.67, 127.77, 126.98, 86.55, 70.76, 70.72, 69.26, 69.08, 63.28, 48.38, 37.61. IR (KBr) 3015, 2932, 2858, 1448, 1356, 1177, 1133, 1085, 921, 718 cm$^{-1}$.

EXAMPLE 2
Preparation and characterization of distearoyl phosphatidyl-choline (DSPC)-PSIDA liposomes PSIDA was cosonicated in aqueous solution with DSPC to prepare mixed small unilamellar vesicles (liposomes). The amounts of DSPC and PSIDA were chosen to provide liposomes having concentrations ranging from 1 to 30 mole percent PSIDA. The cosonication procedure was carried out as follows:

Stock lipid solutions were made by dissolving lipids in CHCl$_3$ (HPLC grade). Lipid 9 and DSPC were combined in varying amounts to make 10 μmoles of total lipid in 12 mL volumetric centrifuge tubes. The lipid mixtures were evaporated under aspirator vacuum, and 3 mL of MOPS buffer [20 mM MOPS, 0.1M NaCl, pH 7.5] was added to the tubes. The tubes were heated above 55° C. and probe tip sonicated (Heat Systems model 375) for 15 minutes at 25–35% power under argon atmosphere in an ice bath. The vesicles were centrifuged at 11,000 rpm for 20 minutes to remove titanium particles. Selected liposome sizes were measured by quasi-elastic light scattering using a Microtrac Ultrafine Particle Analyzer (Leeds & Northrop) at 25° C. in phosphate buffer. The mean diameter was 49 nm (59 nm distribution width for unmetallated vesicles).

Vesicles were diluted 167-fold in MOPS buffer for metal-binding studies. Steady-state fluorescence measurements were performed at 25° C. on a temperature-controlled Shimadzu RF-450 spectrofluorometer, excitation at 346 nm, 5 nm excitation and emission slit width.

Figure 4:
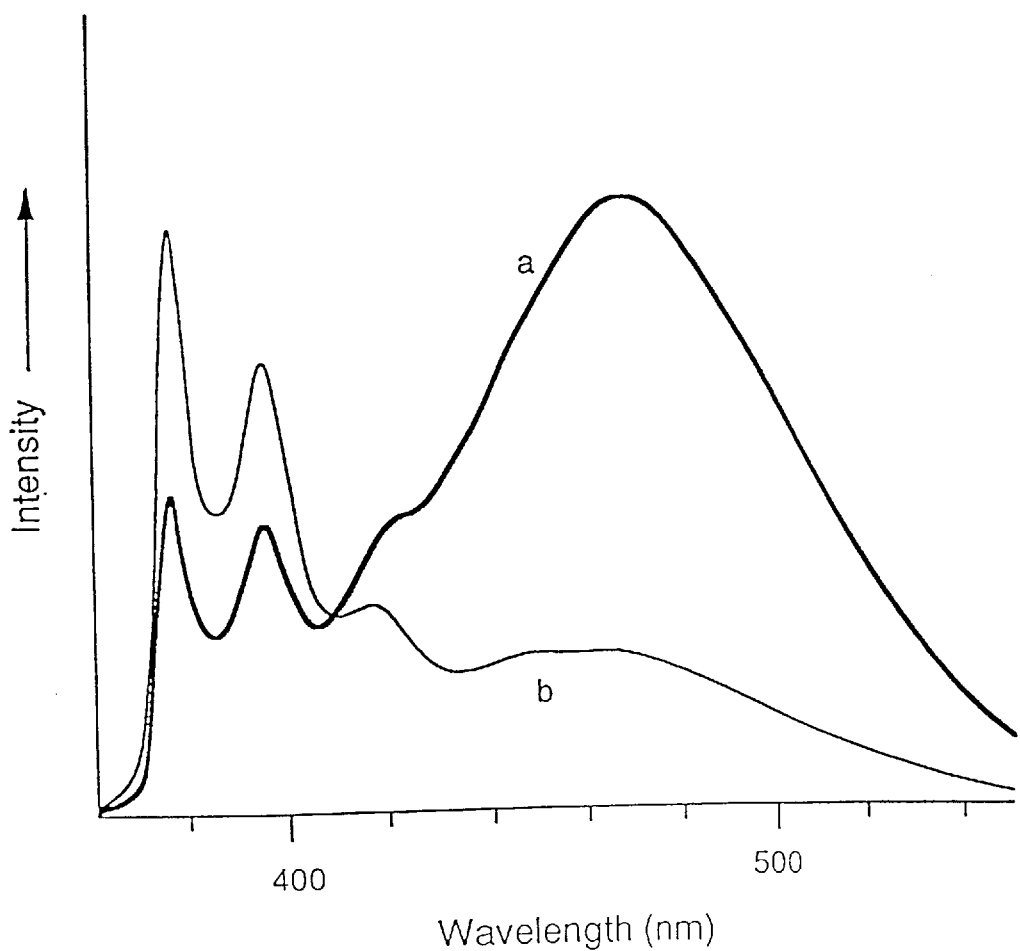
FIG. 4 depicts fluorescence spectra of PSIDA lipid (compound 9 in FIG. 1) in liposomes composed of 5 mol % PSIDA and (a) 95 mol % DSPC and (b) 95 mol % SOPC (1-stearoyl-2-oleoyl-sn-glycero-3-phosphocholine) in 0.1M NaCl, 0.02M MOPS buffer, pH 7.5 and 25° C. The large ratio of the excimer (470 nm) to monomer (377 nm) emission (E/M~1.8) indicates that the PSIDA lipid aggregates in DSPC but not in the more fluid SOPC lipid matrix (E/M~0.2).

The fluorescence spectrum of PSIDA lipid in liposomes of DSPC at 5 mole percent concentration is shown in FIG. 4 as spectrum "a". An excitation wavelength of 346 nm was used. When incorporated in liposomes of DSPC, the PSIDA spectrum "a" includes a typical pyrene monomer emission with a maximum at 377 nm as well as a broad featureless band with a maximum at 470 nm, which is attributed to pyrene excimer. Pyrene collisions are enhanced by confinement of the PSIDA lipid in the two-dimensional DSPC bilayer matrix, yielding a population of excimers. A useful parameter to describe the lateral distribution of pyrene-labeled lipid is the ratio of the excimer to monomer fluorescence intensities, E/M. This parameter is directly related to the collisional frequency of pyrene molecules and therefore is sensitive to the local pyrene concentration. High local concentrations of pyrene in the 5% PSIDA/95% DSPC liposomes at 25° C. are revealed by a high excimer to monomer ratio E/M of 1.8, compared to PSIDA alone in dichloromethane solution. Spectrum b in FIG. 4 depicts the fluorescence of the PSIDA lipid in liposomes composed of 5 mol % PSIDA and 95 mol% SOPC (1-stearoyl-2-oleoyl-sn-glycero-3-phosphocholine). The much lower E/M ratio in the SOPC matrix (E/M~0.2) indicates that the PSIDA lipid is randomly dispersed in the more fluid SOPC lipid matrix.

EXAMPLE 3
Use of PSIDA—DSPC liposomes as a metal ion sensor

Figure 5:
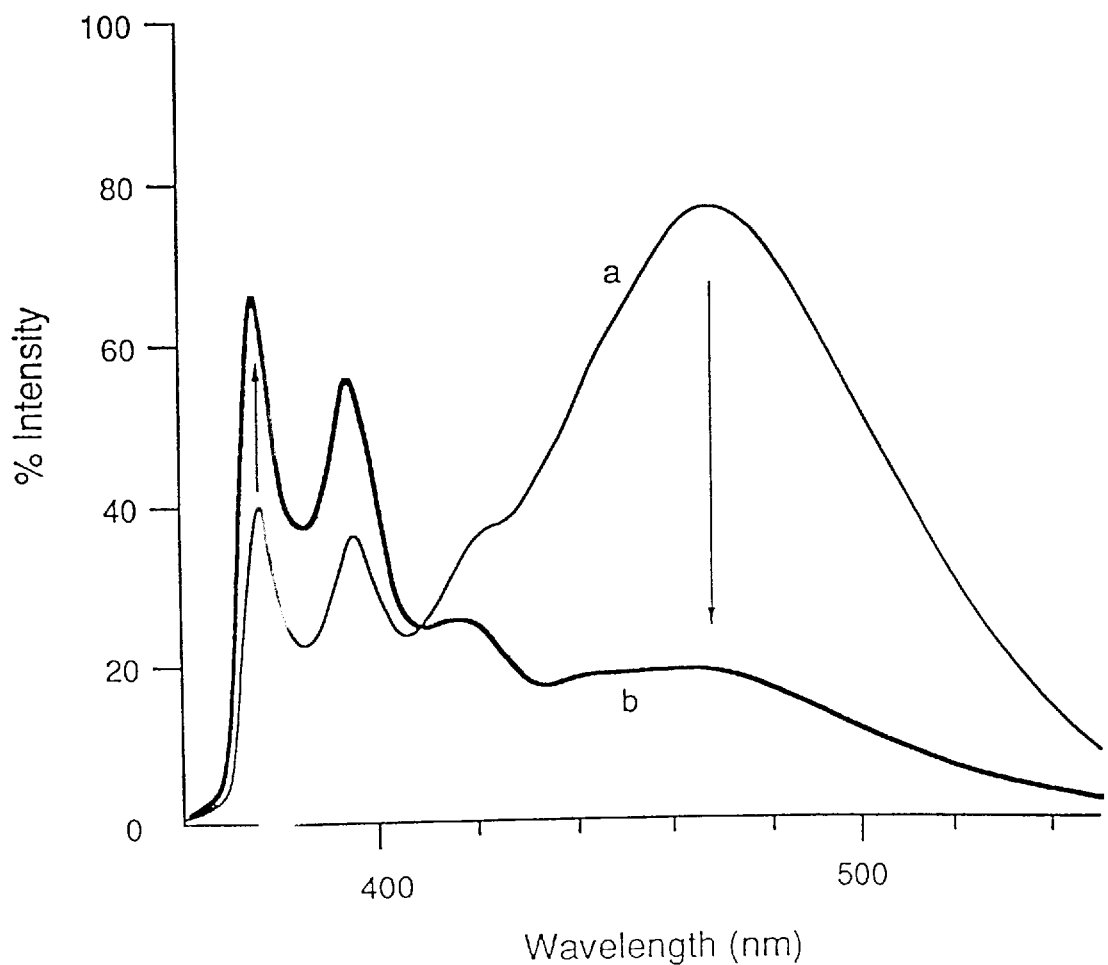
FIG. 5 depicts fluorescence spectra of 5% PSIDA/95% DSPC liposomes in 0.1M NaCl, 0.02M MOPS, pH 7.5 buffer solution before (a) and after (b) addition of 5 μM $Cu^{2+}$, at 25° C. E/M values are 1.80 and 0.27 respectively. Addition of 5 μM $Cu^{2+}$ yields a fluorescence spectrum very similar to that of the 5 mol % PSIDA/95% SOPC liposomes (FIG. 4, curve b), suggesting that the metal ion serves to disperse the PSIDA aggregates. These spectral changes are visible to the naked eye under black light.

Divalent metal ions have a pronounced effect on the fluorescence behavior of PSIDA in DSPC liposomes, decreasing the intensity at 470 nm while increasing the intensity at 377 nm. Addition of metal ions can drive E/M from 1.8 to as low as 0.22. Metal ions have an effect much like that of changing the matrix lipid from a gel to a more fluid material such as SOPC or 50% cholesterol in DSPC. In titration experiments with 5% PSIDA/95% DSPC liposomes at 25° C., pH 7.5, it was observed that the excimer emission intensity decreases, while the monomer emission increases with increasing metal concentration. FIG. 5 shows fluorescence spectra of 5 mole % PSIDA/95% DSPC liposomes in 0.1M NaCl, 0.02M MOPS, pH 7.5 buffer solution before (a) and after (b) addition of 5 82 M Cu$^{2+}$, at 25° C. E/M values are 1.80 and 0.27, respectively. As can be seen from FIG. 5, the PSIDA/DSPC liposomes are effective as a fluorescent sensor for copper ions, particularly at 377 and 470 nm.

Figure 6:
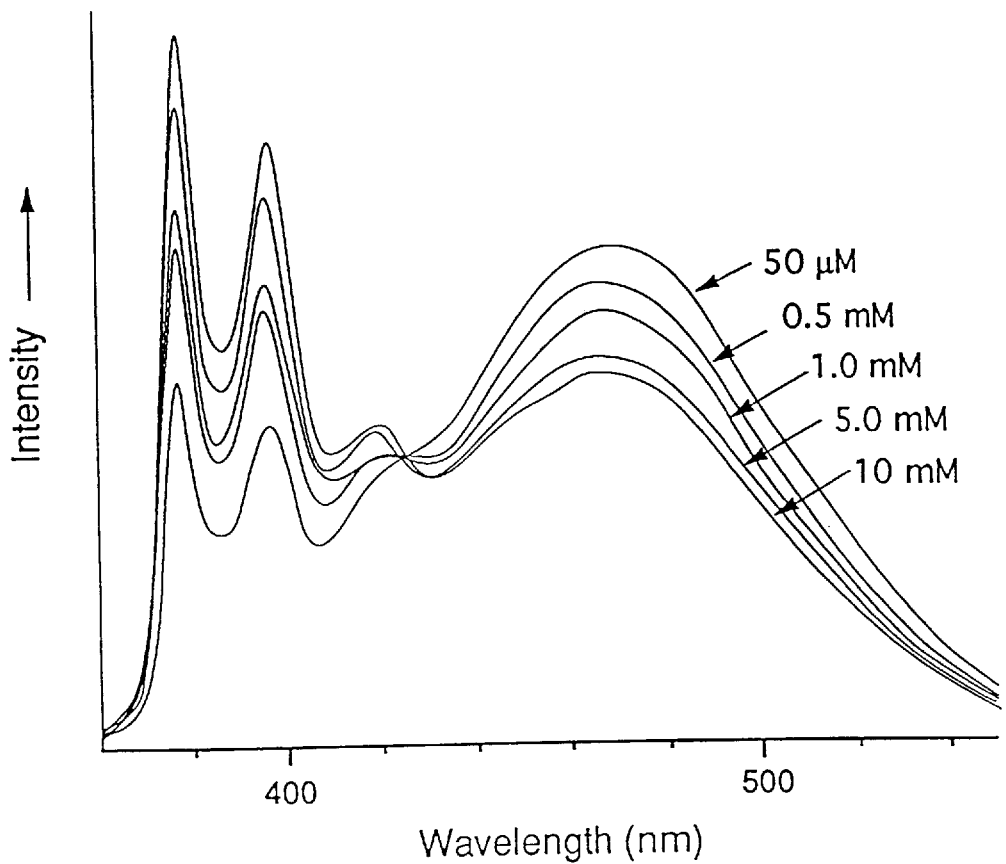
FIG. 6 depicts the fluorescence emission spectra of 5% PSIDA/95% DSPC vesicles in [0.02M MOPS, 0.1M NaCl, pH 7.5] buffer at 25° C., titrated with increasing concentrations of $MnCl_2$.
Figure 7:
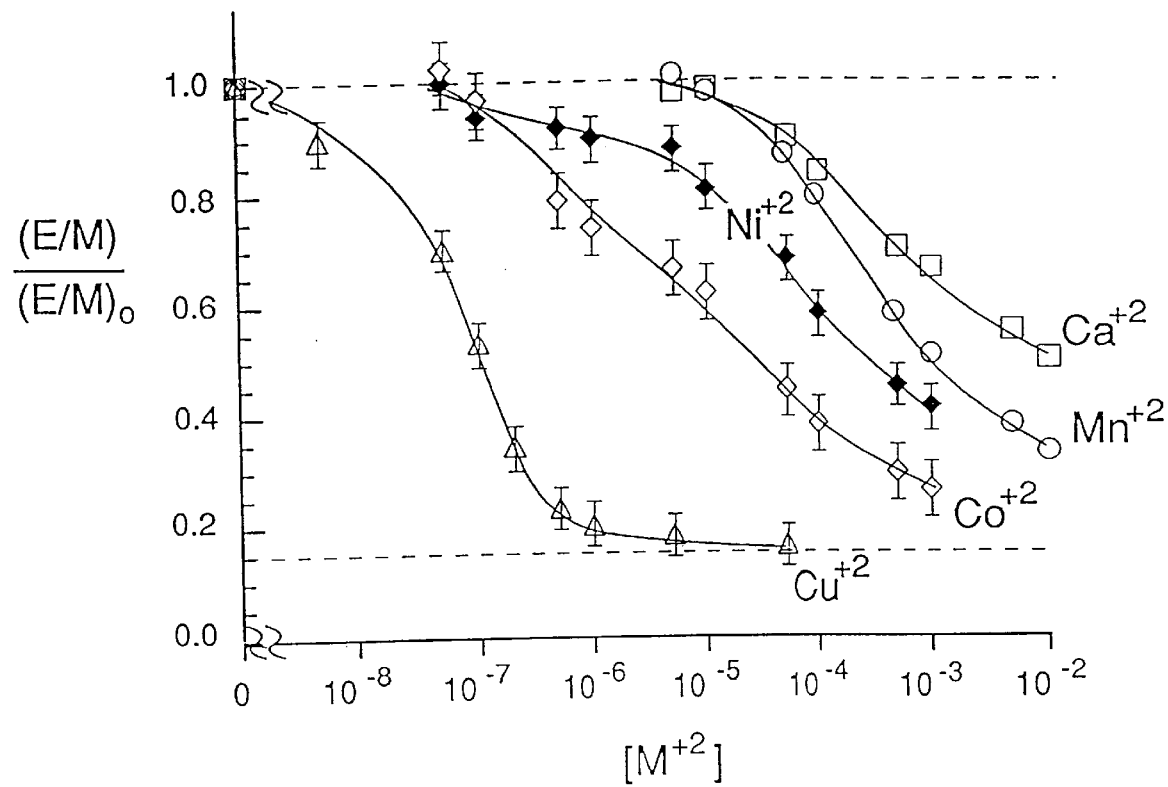
FIG. 7 depicts the fluorescence E/M values (normalized by E/M without added metal) for 5% PSIDA/95% DSPC vesicles, 0.11 μM total lipid, in the presence of various metal ions at 25° C. The metals were added as the chloride salts in 0.1M NaCl. Curve fits are for the benefit of the reader.

Typical fluorescence metal ion titration spectra (Mn$^{2+}$) for these liposomes are presented in FIG. 6. The presence of the isosbestic point at 425 nm reveals a population inversion of excimers and monomers. Titration with other metal ions induces similar behavior, but at different metal concentrations. FIG. 7 shows the normalized E/M values as a function of metal ion concentration for a number of different metals. The curves reflect sensitivities to the metals in generally the same order as their binding constants to methoxyethylimi-nodiacetic acid. As is apparent from FIG. 7, the PSIDA aggregates are most sensitive to CU$^{2+}$.

Figure 8:
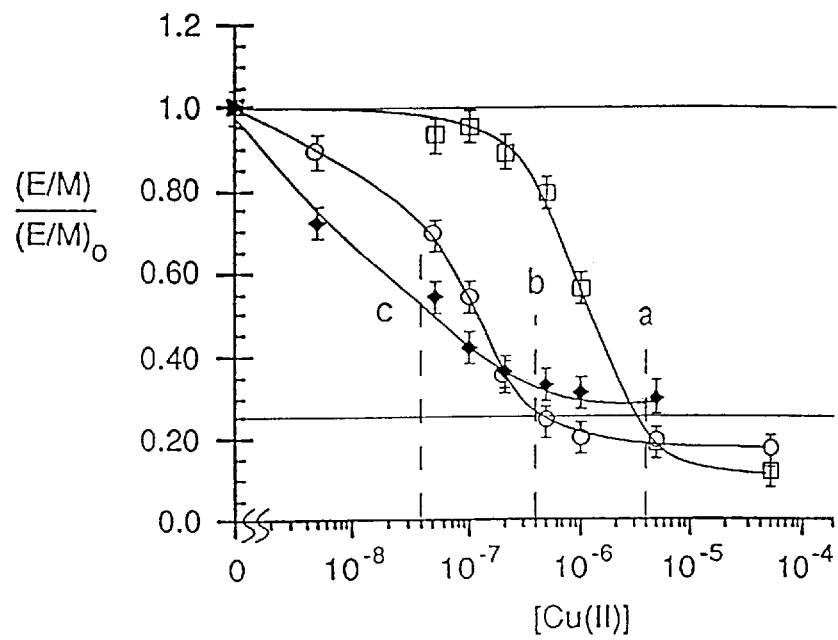
FIG. 8 shows the effect of $Cu^{2+}$ on the fluorescence E/M (normalized to E/M with no metal added) of 5% PSIDA/95% DSPC liposomes at concentrations of 65 μM (□), 6.5 μM (○), and 650 nM (♦) total phospholipid at 25° C. Equivalence points of metal ion to PSIDA lipid are shown as dashed lines and correspond to the concentration of PSIDA lipid: (a) 3.5 μM, (b) 350 nM, and (c) 35 nM. The E/M changes of 5% PSIDA/95% DSPC liposomes at 650 nM total phospholipid concentration show that this system is sensitive to $Cu^{2+}$ at nanomolar concentrations.

To demonstrate the limit of sensitivity for the PSIDA-DSPC sensor, $Cu^{2+}$ was titrated into liposome solutions containing lower total lipid concentrations, the results of which are shown in FIG. 8. In FIG. 8, the effect of $Cu^{2+}$ on the E/M of 5% PSIDA/95% DSPC liposomes at concentrations of 65 $\mu$M (□), 6.5 $\mu$M (○), and 650 nM (♦) total phospholipid, is shown. Equivalence points of metal ion to PSIDA lipid are shown as dashed lines and correspond to the concentration of PSIDA lipid: (a) 3.5 $\mu$M, (b) 350 nM, and (c) 35 nM. For the two higher lipid concentrations, 6.5 and 65 $\mu$M, a saturation effect is observed beginning from the equivalence point of metal ion to PSIDA. This implies that the PSIDA concentration (~3 $\mu$M) is large compared to the dissociation constant $K_d$ of $Cu^{2+}$ to the liposome. The sensor was sensitive to 5 nM $Cu^{2+}$ (less than 1 part per billion) with the above conditions.

All of the above described metal induced effects were found to be completely reversible by the addition of EDTA. Further, the addition of EDTA did not alter the liposome structure.

As is apparent from the above examples, the PSIDA/DSPC mixed bilayer system exhibits a selectivity for different metal ions with high sensitivity down to the nanomolar range with $Cu^{2+}$. Due to the strong binding constant of IDA, this bilayer system exhibits high sensitivity and selectivity for $Cu^{2+}$. The selectivity allows nanomolar concentrations of $Cu^{2+}$ ion to be detected in a solution containing 0.1M NaCl and millimolar concentrations of $Ca^{2+}$, for example. Moreover, the fluorescence color change can be followed by the naked eye in black light with detection limits down to sub-micromolar $Cu^{2+}$ concentrations. The system can also be completely regenerated by the addition of EDTA. With a response time of seconds and these aforementioned properties the PSIDA/DSPC liposomes may be used as a $Cu^{2+}$ sensor system.

EXAMPLE 4
E/M Behavior Of PSIDA/DSPC Liposomes

The E/M behavior of PSI DA/DSPC liposomes prepared as in Example 3 with varying mole fractions of PSI DA was studied at temperatures above and below the $T_c$ of DSPC (55° C.). The results are summarized in Table 1. As expected, E/M increased with increasing PSIDA mole fraction at all three temperatures. No change was observed in the maximum wavelengths of either the excimer or monomer emissions with increasing PSIDA mole fraction.

TABLE 1

| | E/M[b] | | | | | |
|---|---|---|---|---|---|---|
| | 25° C. | | 40° C. | | 60° C. | |
| % PSIDA/DSPC[a] | initial[c] | $Cu^{2+}$[d] | initial | $Cu^{2+}$ | initial | $Cu^{2+}$ |
| 1 | 0.32 | 0.17 | 0.44 | 0.15 | 0.47 | 0.16 |
| 2 | 0.59 | 0.18 | 0.55 | 0.16 | 0.33 | 0.19 |
| 5 | 1.23 | 0.33 | 1.76 | 0.37 | 0.66 | 0.38 |
| 10 | 2.06 | 0.40 | 2.18 | 0.72 | 0.86 | 0.56 |
| 20 | 4.58 | 1.63 | 4.14 | 2.16 | 2.30 | 1.38 |

[a])Initial molar percent in liposome preparations.
[b])Fluorescence intensities of excimer to monomer measured at 470 nm (excimer) and 377 nm (monomer).
[c])Fluorescence measurement of mixed liposomes in 0.1M NaCl, 0.02M MOPS buffer at pH 7.5.
[d])Fluorescence measurements of initial condition with addition of 10 $\mu$M $CuCl_2$.

Table 1 also summarizes the effects of 10 $\mu$M $Cu^{2+}$ on the E/M of the PSIDA/DSPC liposomes at the various temperatures. At 25° C. and 40° C. below the $T_c$ of DSPC, $Cu^{2+}$ induces a large change in E/M at all PSIDA/DSPC compositions. At 60° C., which is above the $T_c$ of DSPC, the PSIDA should be more fully dispersed in the matrix lipid. Addition of $Cu^{2+}$ has a much smaller, but still significant, effect on the E/M at this temperature.

EXAMPLE 5
Metal Titration Studies With Different Pyrene-Labeled Lipids

Figure 9:
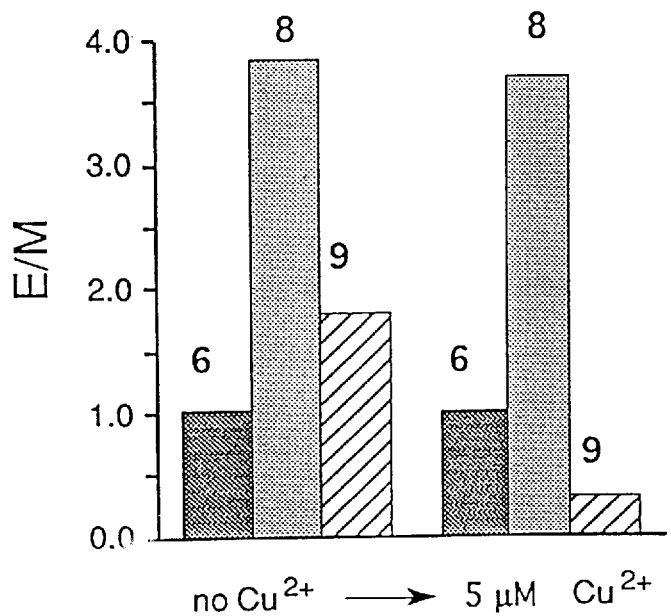
FIG. 9 is a bar graph indicating E/M values of liposomes containing 5 mol % lipids 6,8 or PSIDA (9 in FIG. 1) and 95 mol % DSPC at 25° C. Bars on the left represent the fluorescent E/M before addition of $Cu^{2+}$, and bars on the right are the E/M values observed in the presence of 5 μM $Cu^{2+}$. The liposomes containing the metal-chelating fluorescent lipid 9 show a dramatic change in E/M upon addition of $Cu^{2+}$, while very little changes are seen for liposomes containing non-metal-chelating lipids 6 and 8.

Metal titration studies were also performed with non-metal-chelating pyrene lipids (6 and 8 in FIG. 1) in DSPC liposomes. These tests were done to confirm that the effects observed with PSIDA are due to specific metal chelation by that lipid rather than metal-induced fluorescence quenching or metal-induced membrane perturbation. Lipids 6 and 8 have alcohol and diethyliminodiacetate headgroups, respectively, linked to a lipid structure that is otherwise identical to PSI DA. Both 6 and 8 were prepared in 5% lipid/95% DSPC liposomes, and their fluorescence E/M are compared to liposomes containing PSIDA (9) in FIG. 9. Of the three mixed liposomes, lipid 6 has the lowest E/M at 1.0, PSIDA has a value of 1.8, and lipid 8 has the highest, at 3.7. While addition of $Cu^{2+}$ at 5 $\mu$M concentration induces a large change in the fluorescence of the PSIDA/DSPC liposomes, very little change is seen for the liposomes containing 6 and 8. Even at 1000×higher concentrations of $Cu^{2+}$ (mM), essentially no change in fluorescence E/M or intensity was observed for liposomes containing 6 and 8.

Although it is known that metal ions can perturb lipid membranes or quench pyrene fluorescence, the above results show that the metal-induced E/M changes are not a by product of these processes. The above studies performed with non-metal binding lipids 6 and 8 showed that metal ions do not cause lipid aggregation changes by directly perturbing the membrane in a nonspecific manner. Only the system containing lipid 9, with a metal-chelating headgroup shows a significant metal-induced change in fluorescence.

Fluorescence quenching by $Cu^{2+}$ ion is observed with PSIDA in fluid bilayers of SOPC at 25° C. and DSPC above its $T_c$. The high ion permeability of these fluid bilayers allows pyrene-ion contact and quenching to occur in the bilayer. In the ion impermeable gel phase of DSPC or DSPC/cholesterol bilayers the pyrene fluorophore is effectively shielded in the bilayer from quenching. This is manifest in studies with 6 and 8 in DSPC liposomes. The chelation of metal ions at the membrane surface, as would be expected with PSIDA/DSPC bilayers, does not appear to have any metal quenching effect, either. Furthermore, ions that are not known to quench pyrene fluorescence (i.e. $Ca^{2+}$) effects the same E/M reduction for PSIDA/DSPC bilayers as do metals known to quench fluorescence (FIG. 7).

EXAMPLE 6
Effect Of Using Different Matrix Lipids

The process of Example 2 was repeated using PSIDA and matrix lipids similar to DSPC, but with varying lengths of their aliphatic tails, to prepare mixed liposomes to test their use as metal ion sensors. Thus, 5 mol % PSIDA was mixed with 95% matrix lipid containing acyl chains with between 12 and 22 carbon units: dilauroylphosphatidylcholine (DLPC), dimyristoylphosphatidylcholine (DMPC), dipalmitoylphosphatidylcholine (DPPC), diarachidoylphosphatidylcholine (DAPC), and dibehenoylphosphatidylcholine (DBPC). The process of Example 3 was repeated to determine the sensitivity of the fluorescence spectra to metal ion concentration. For matrix lipids with acyl chains smaller than 16 carbons (DMPC, DLPC), the decrease in E/M ratio in the presence of copper is not substantial and resembles the changes seen for unsaturated lipids like SOPC. 5% PSIDA/ 95% DMPC liposomes, for example, showed only a small E/M change from 0.3 to 0.2 upon addition of 1.5 $\mu$M $CuCl_2$.

Figure 11:
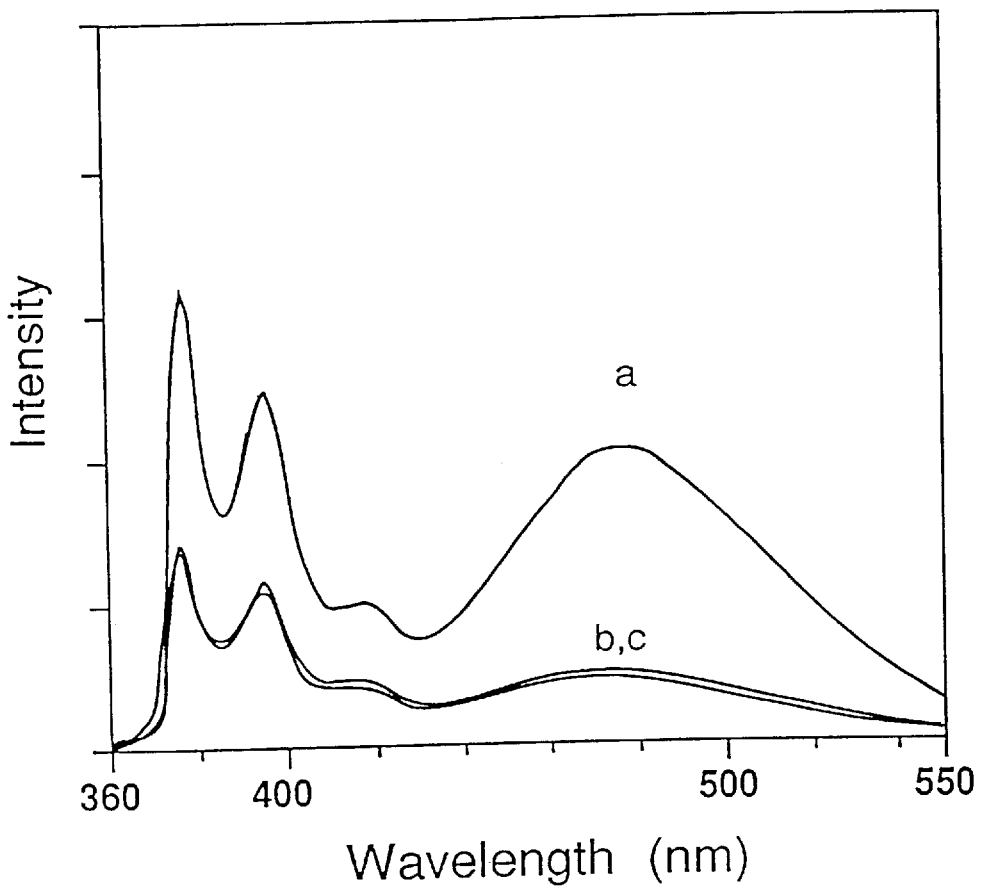
FIG. 11 depicts fluorescence spectra of 5% PSIDA/95% DPPC liposomes in 0.1M NaCl, 0.02M MOPS, pH 7.5 at 25° C.: (a) No metal ions added; (b) after addition of 0.75 μM $CuCl_2$; (c) after addition of 1.5 μM $CuCl_2$.

FIG. 11 shows the fluorescence spectra (using an excitation wavelength of 346 nm) of liposomes containing 5 mol % PSIDA lipid (9) and 95 mol % DPPC comprising a sensor prepared as in Example 2. After cosonication of the matrix lipid and the metal-chelating fluorescent amphiphile (PSIDA), the liposomes were diluted 100-fold in MOPS buffer [0.02M MOPS, 0.1M NaCl, pH 7.5] in a quartz cuvette. The emission intensity due to excimers (470 nm) is lower than for liposomes prepared using DSPC as the matrix lipid. Nevertheless, a decrease in fluorescence excimer emission intensity results upon metal ion binding. In FIG. 11 curve (a) shows a large population of excimer aggregates, with a strong emission at 470 nm. Curve (b) corresponds to a $Cu^{2+}$ concentration of 0.75 $\mu$M, while (c) corresponds to a $Cu^{2+}$ concentration of 1.5 $\mu$M, showing that the effect is already saturated at less than 1 $\mu$M concentration. The accompanying decrease in the monomer emission intensity may be due to aggregation of the liposomes at this relatively high liposome concentration.

Figure 12:
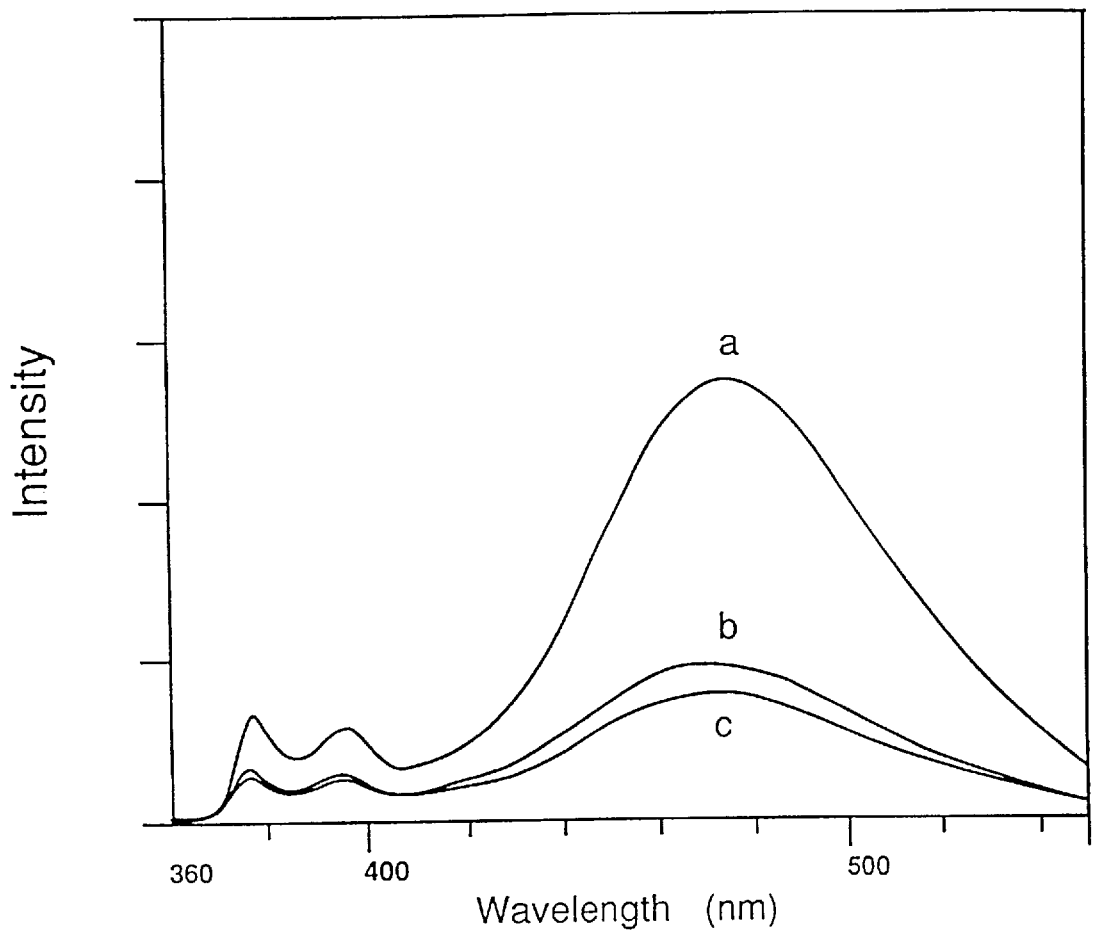
FIG. 12 depicts fluorescence spectra of 5% PSIDA/95% DBPC liposomes in 0.1M NaCl, 0.02M MOPS, pH 7.5 at 25° C.: (a) No metal ions added; (b) after addition of 0.75 μM $CuCl_2$; (c) after addition of 1.5 μM $CuCl_2$. The respective E/M values for curves (a) and (c) are 4.3 and 2.9.

The metal sensor also works well using matrix lipids containing acyl chains longer than the 18 carbon units of DSPC. DBPC has acyl chains containing 22 carbons. DBPC/PSIDA liposomes initially have a higher E/M value (before metallation) than do DSPC/PSIDA liposomes. As shown in FIG. 12, metal binding caused the E/M ratio to decrease significantly, from 4.3 to 2.9, similar to the behavior of the PSIDA/DPPC sensor described above and the PSIDA/DSPC sensor described in Example 3. DAPC has acyl chains containing 20 carbons. A decrease in the E/M ratio from 0.9 to 0.5 was observed upon addition of metal ions to liposomes made using DAPC as the matrix lipid.

The fluorescence excimer emission remaining after exposure to metal was higher for matrix lipids with>22-carbon acyl chains. Because the solubility of a matrix lipid in water decreases with increasing chain length, lower concentrations of liposomes can be obtained using these lipids. Thus matrix lipids with longer acyl chains are preferred for sensing applications requiring very low detection limits. The optimal matrix lipid chain length for use with a given metal-chelating fluorescent amphiphile can be determined by forming the mixed liposomes, diluting them to the appropriate concentration, and measuring the change in fluorescent excimer emission intensity, as described in this Example.

EXAMPLE 7
Preparation Of DSPA-PSIDA Lipid-Based Metal Ion Sensor

Figure 13:
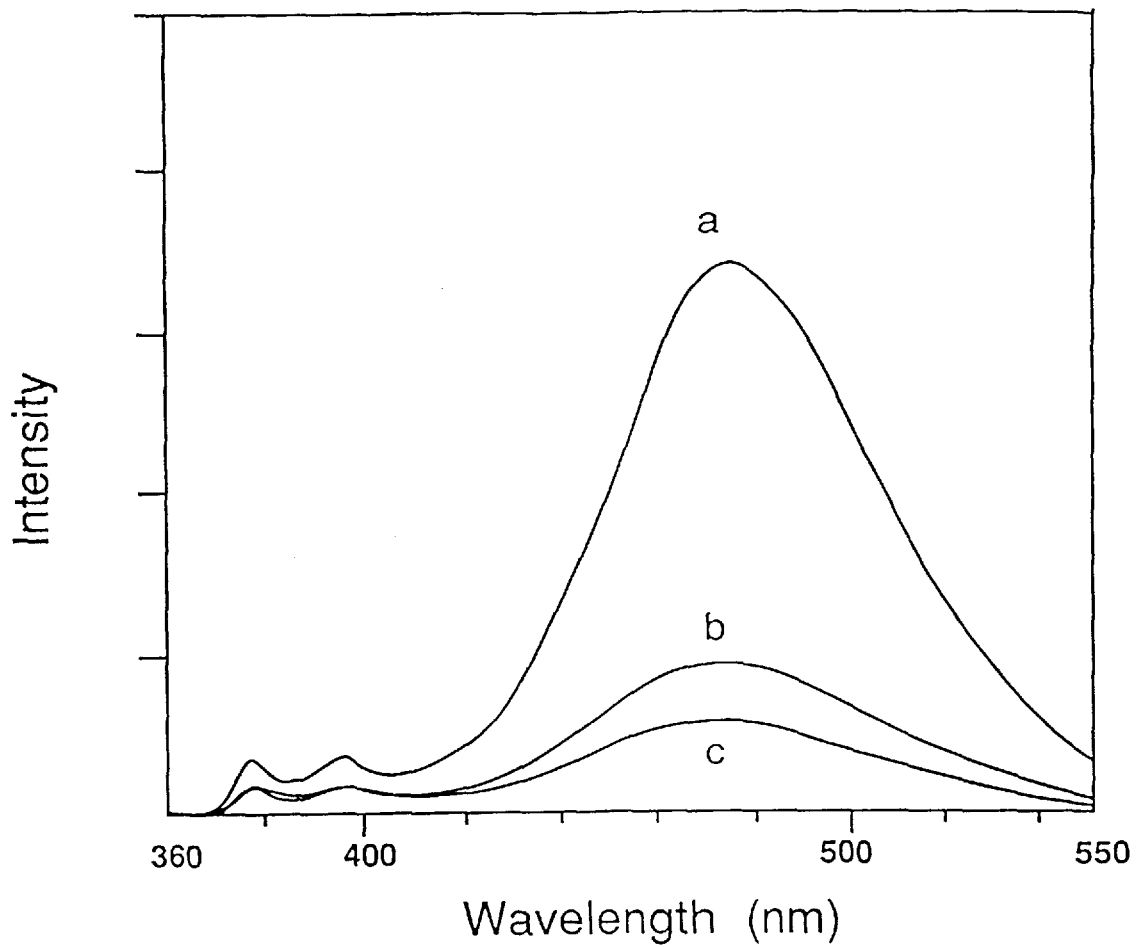
FIG. 13 depicts fluorescence spectra of 5% PSIDA/95% DSPA liposomes in 0.1M NaCl, 0.02M MOPS, pH 7.5 buffer at 25° C.: (a) No metal ions added; (b) after addition of 0.75 μM $CuCl_2$; (c) after addition of 1.5 μM $CuCl_2$. The respective E/M values for curves (a) and (c) are 7 and 3.

The process of Example 6 was repeated using PSIDA and a negatively charged matrix lipid, distearoylphosphatidic acid (DSPA), to prepare mixed liposomes and assess their utility as a lipid-based metal ion sensor. The charge of the matrix lipid head group is expected to influence the solubility of the liposomes, the pH range of operation, and to affect the pH dependence of changes in the fluorescence spectra upon metal binding. FIG. 13 (curve a) shows the strong excimer emission intensity (470 nm) of mixed liposomes containing 5 mol % PSIDA and 95 mol % DSPA. This fluorescence intensity decreases dramatically in the presence of copper ions (curves b, c), and, as in Examples 5 and 6, the effect is strongest at the excimer wavelength.

In the liposomes containing negatively charged DSPA matrix lipid there is a relatively large population of excimers, as evidenced by the high initial E/M value (curve a). This sensor showed a decrease in the E/M ratio from 7 to 3 after addition of approximately 1:1 metal ions to PSIDA in the sample. Further addition of copper resulted in precipitation of the liposomes. Negatively charged liposomes are known to crosslink with divalent metal ions and consequently precipitate.

EXAMPLE 8
Synthesis Of Pyrene Stearyl Cyclam (PS-Cyclam)

Figure 14:
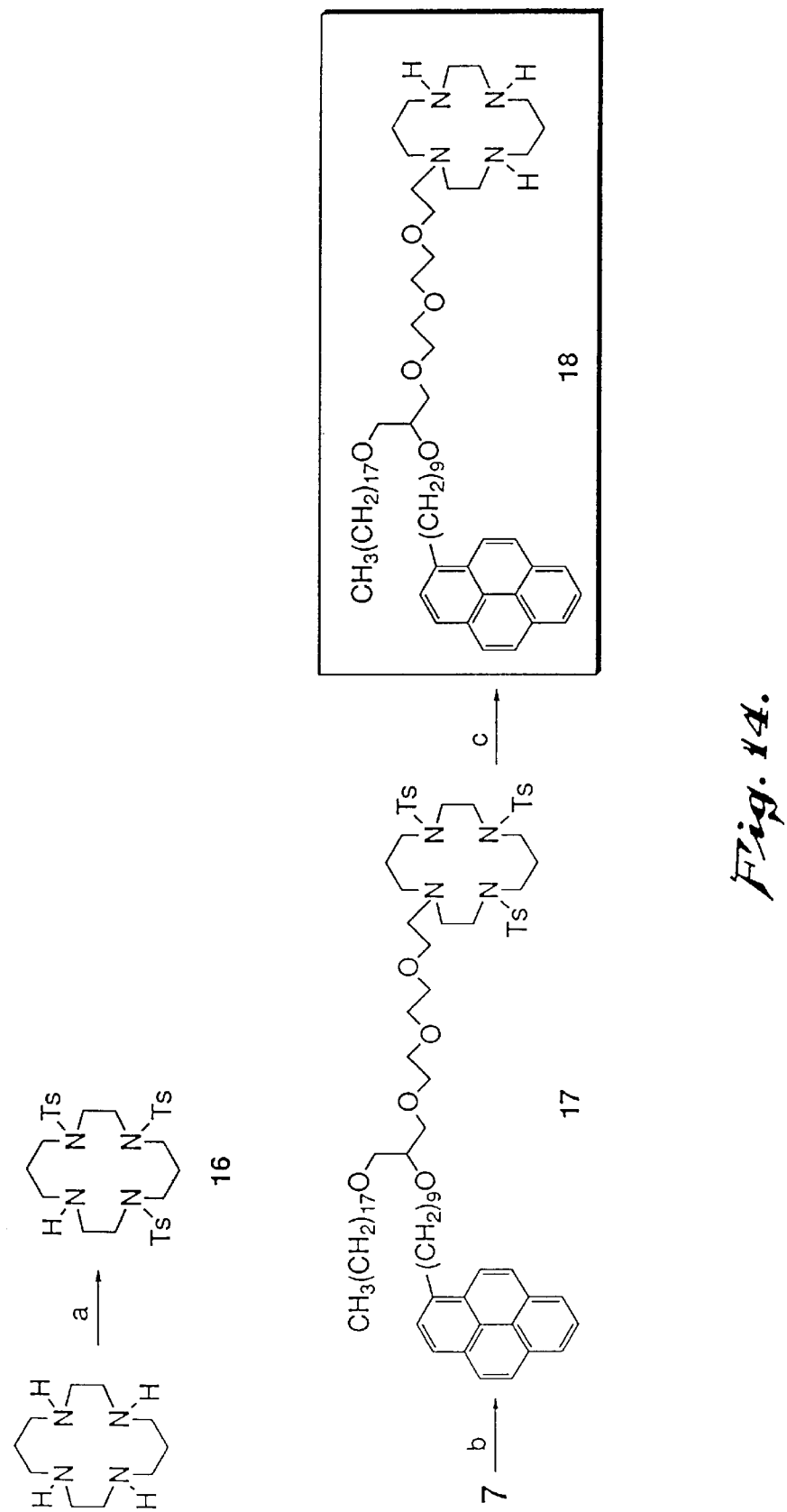
FIG. 14 is a diagram of the synthesis scheme for making an exemplary metal-chelating fluorescent lipid, pyrene stearyl cyclam (PS-cyclam), in accordance with the present invention.

The metal-chelating fluorescent lipid pyrene stearyl cyclam (PS-cyclam) was synthesized in accordance with the present invention in the sequence outlined in FIGS. 1 and 14.

Preparation of 1,4,8-tritoluenesulfonyl-1,4,8,11-tetraazacyclotetradecane (16) is shown as step "a" in FIG. 14. To a solution of tetraazacyclotetradecane (1.00 g, 5.0 mmole) and $NEt_3$ (2.1 mL, 1.5 g, 15.0 mmole) in $CH_2Cl_2$ (20 mL) was added dropwise toluenesulfonyl chloride (1.90 g, 10.0 mmol) in $CH_2Cl_2$ (20 mL). After complete addition of toluenesulfonyl chloride, the originally heterogeneous solution became homogenous. The reaction was then stirred 15 hours at room temperature. The solution was diluted with $CH_2Cl_2$ (30 mL) and $H_2O$ (70 mL), the mixture shaken, layers separated, and the aqueous layer further extracted with fresh $CH_2Cl_2$ (2×40 mL). The organics were combined and washed with $H_2O$ (60 mL) then aq. sat. NaCl (50 mL), followed by drying over anhydrous $MgSO_4$, filtered, and concentrated in vacuo. The residuals were flash column chromatographed with $MeOH/CH_2Cl_2$ (4% v/v, $R_f$=0.25). Product 16 was obtained (1.20 g, 36%). $^1H$ NMR $\delta$7.76–7.58 (m, 6H), 7.38–7.16 (d, J=8.3 Hz, 6H), 3.42–3.00 (m, 12H), 2.85–2.74 (m, 2H), 2.72–2.54 (m, 2H), 2.48 (s, 6H), 2.44 (s, 3H), 2.08–1.94 (m, 2H), 1.80–1.68 (m, 2H).

Preparation of 3-octadecyloxy-2-(9-(1-pyrene)nonyloxy)-propan-1-(9-(3,6,9-trioxynonyl-1-(4,8,11-tritoluenesulfonyl-1,4,8,11-tetraazacyclotetradecane))) (17) is shown as step "b" in FIG. 14. Compound 7 (0.8 g, 0.9 mmole), compound 16 (0.87 g, 1.3 mmole) and $K_2CO_3$ (0.3 g, 2.2 mmole) were placed in THF (8 mL)/$CH_3CN$ (10 mL) solution and refluxed for 5 days. The reaction mixture was cooled to room temperature, concentrated in vacuo, and flash column chromatographed with $Et_2O/CH_2Cl_2$ (15% v/v, $R_f$=0.34). Product 17 was obtained (0.62 g, 46%). $^1H$ NMR $\delta$8.28 (d, J=9 Hz, 1H, Py—H), 7.95–8.17 (m, 7H), 7.86 (d, J=8H, 1H, Py—H), 2.65–2.48 (m, 4H), 2.43 (s, 6H), 2.41 (s, 3H), 1.94–1.70 (m, 4H), 1.60–1.24 (m, 46H), 0.87 (t, J=6.9 Hz, 3H).

Preparation of 3-octadecyloxy-2-(9-(1-pyrene)nonyloxy)-propan-1-(9-(3,6,9-trioxynonyl-1-tetraazacyclotetradecane)) (18) is shown as step "c" in FIG. 14. Compound 17 (0.74 g, 0.51 mmole) and $NaAlH_2$ $(OCH_2CH_2CH_3)_2$ (1.24 g, 6.1 mmole) were placed in dry toluene (15 mL) and refluxed for 22 hours. The reaction mixture was cooled to room temperature and 10% of NaOH aqueous solution (20 mL) was added to quench the reaction which was then extracted with fresh $Et_2O$ (50 mL). The organic solution was further washed with 10% NaOH (50 mL), $H_2O$ (50 mL) and aq. sat. NaCl (50 mL). Then the mixture was shaken, layers separated and aqueous layer extract with fresh $Et_2O$ (2×50 mL). The organics were combined, washed with aq. sat. NaCl (30 mL), followed by drying over anhydrous $MgSO_4$, filtered, and concentrated in vacuo to yield 18. $^1H$ NMR $\delta$8.28 (d, J=9 Hz, 1H, Py—H), 8.20–7.92 (m, 7H), 7.85 (d, J=8.3 Hz, 1H, Py—H), 3.74–3.20 (m, 25H), 2.84–2.52 (m, 10H), 1.92–1.76 (m, 3H), 1.62–1.00 (m, 54H), 0.84 (t, J=6.9 Hz, 3H).

EXAMPLE 9
Preparation Of Naphthyl Stearyl Iminodiacetic Acid (NSIDA)

Figure 15:
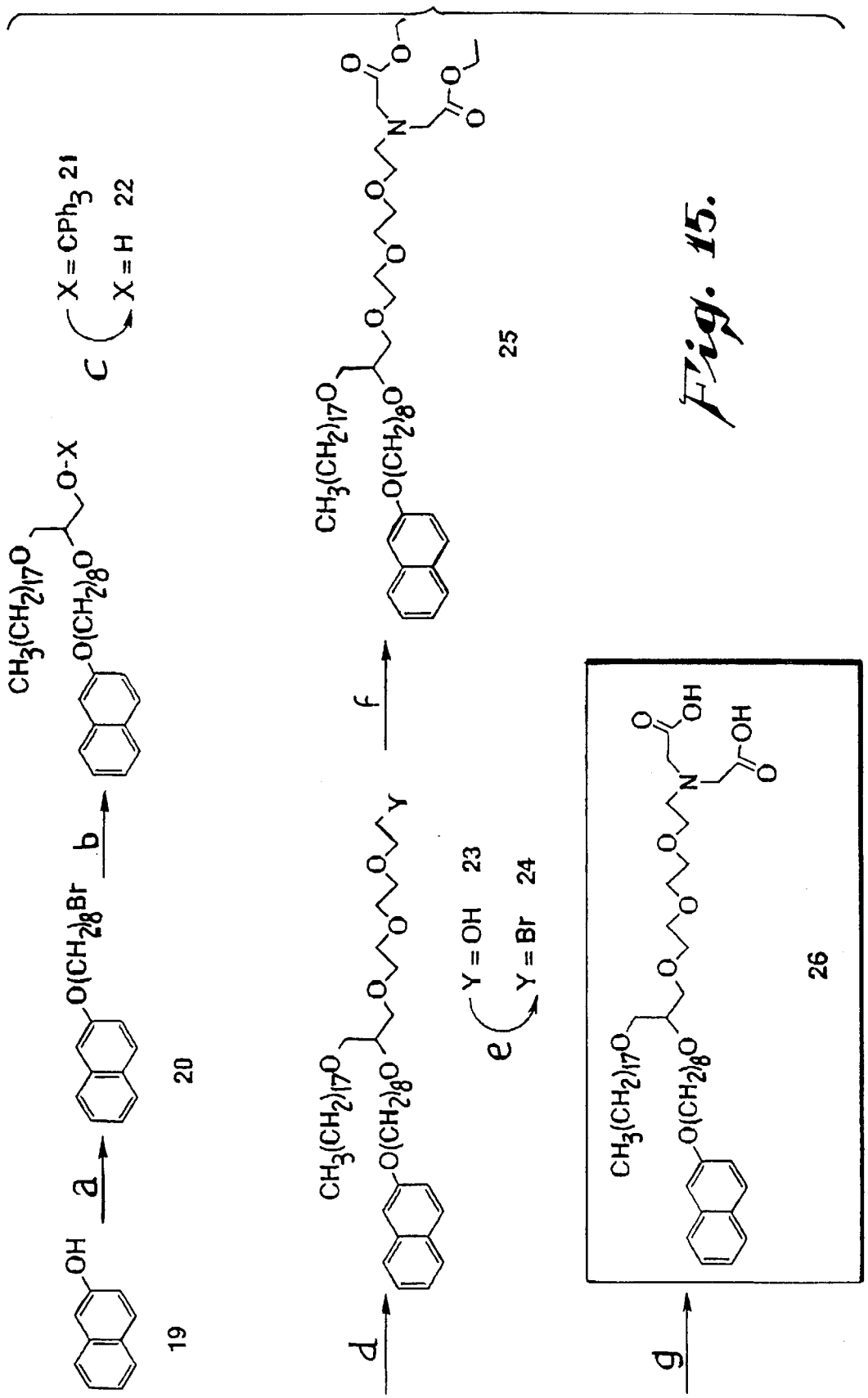
FIG. 15 is a diagram of the synthesis scheme for making an exemplary metal-chelating fluorescent lipid, naphthyl stearyl IDA (NSIDA), in accordance with the present invention.

The metal-chelating fluorescent lipid naphthyl stearyl iminodiacetic acid (NSIDA) (compound 26 in FIG. 15) was synthesized in accordance with the present invention in the sequence outlined in FIG. 15.

Preparation of 8-(naphthyl-2-oxy)-1-bromooctane (20) is shown as step "a" in FIG. 15. 19 (4.00 g, 27.7 mmole), $Br(CH_2)_8Br$ (11.3 g, 41.5 mmole) and powdered KOH (3.11 g, 55.4 mmole) were placed in DMSO (70 mL) and stirred for 1 hour at 70° C. After the initial bluish-green color had turned to pale yellow color (1 hour reaction time), the solution was cooled to room temperature then diluted with 130 mL of $Et_2O$ and 150 mL water. This mixture was shaken, then 60 mL $CH_2Cl_2$ was added. The layers were separated and the aqueous phase was extracted twice with 70 mL ethyl acetate. The combined organic layers were filtered to remove the precipitate which formed during extraction, followed by washing with water (2×100 mL) and 100 mL aq. sat. NaCl solution. The solution was then dried over anhydrous $MgSO_4$ and the solvent removed in vacuo. The residue was taken up in 70 mL $Et_2O$ and this solution was filtered to remove any insoluble solids. This mixture was chromatographed with $CH_2Cl_2$/hexanes (20% v/v, $R_f$=0.31) to yield the product (4.92 g, 50%). $^1H$ NMR δ7.74 (m, 3H, Np—H), 7.43 (dd, J=7.0, 7.3 Hz, 1H, Np—H), 7.32 (dd, J=7.2, 7.0 Hz, 1H, Np—H), 7.12 (m, 2H, Np—H), 4.07 (t, J=6.5 Hz, 2H, —OCH$_2$), 3.41 (t, J=6.8 Hz, 2H, —CH$_2$Br), 1.84 (m, 4H, —OCH$_2$CH$_2$, CH$_2$CH$_2$Br), 1.46 (m, 8H). $^{13}C$ NMR δ157.00, 134.54, 129.27, 128.80, 127.59, 126.64, 126.25, 123.42, 118.97, 106.42, 67.84, 34.04, 32.75, 29.18, 28.67, 28.07, 25.99. IR (KBr) 3058, 2932, 2852, 1630, 1601, 1469, 1260, 1221, 1186, 840 cm$^{-1}$. Anal.: Calcd for $C_{18}H_{23}OBr$: C, 64.48; H, 6.91. Found: C, 64.78; H, 7.14.

Preparation of 1-octadecyl-2-(8-(naphthyl-2-oxy)-1-octyl)-rac-glycero-3-triphenylicarbine (21) is shown as step "b" in FIG. 16. 3 (2.00 g, 3.41 mmole), 20 (1.60 g, 4.78 mmole) and powdered KOH (0.57 g, 10.2 mmole) were placed in dry DMSO and stirred at 80° C. overnight. The solution was then cooled to room temperature and diluted with 70 mL of $Et_2O$ and 100 mL water. This mixture was shaken and the layers separated. The aqueous layer was then shaken twice with 70 mL $Et_2O$. The combined organic layers were then washed twice with 100 mL water and once with 70 mL aq. sat. NaCl solution. The solution was dried over anhydrous $MgSO_4$ and the solvent was removed in vacuo. The material was chromatographed with $CH_2Cl_2$/hexanes (50% v/v, $R_f$=0.30) to yield the product (2.05 g, 72%). $^1H$ NMR δ7.72 (m, 3H, Np—H), 7.43 (m, 7H, Np—H, Ph—H), 7.27 (m, 10H, Np—H, Ph—H), 7.15 (m, 2H, Np—H) 4.03 (t, J=6.5 Hz, 2H, Np—OCH$_2$), 3.53 (m, 5H, —OCH), 3.39 (t, J=6.5 Hz, 2H, —OCH$_2$), 3.17 (br d, 2H, CH$_2$OPh$_3$), 1.82 (m, 2H, Np—OCH$_2$CH$_2$), 1.58–1.25 (m, 42H, aliphatic CH$_2$), 0.88 (t, J=5.9 Hz, 3H, —CH$_3$). $^{13}C$ NMR δ157.06, 144.13, 134.58, 129.26, 129.11, 128.72, 128.47, 127.92, 127.70, 127.62, 127.08, 126.87, 126.66, 126.24, 123.40, 119.01, 106.43, 86.46, 78.29, 71.60, 71.13, 70.64, 67.93, 63.57, 31.94, 30.11, 29.71, 29.54, 29.42, 29.25, 26.10, 22.71, 14.16. IR (KBr) 3058, 2924, 2852, 1629, 1600, 1465, 1257, 1217, 1181, 1119, 706 cm$^{-1}$.

Preparation of 1-octadecyl-2-(8-(naphthyl-2-oxy)-1-octyl)-rac-glycerol (22) is shown as step "c" in FIG. 15. 21 (2.00 g, 2.38 mmole) was placed in a mixture of THF (7 mL)/methanol (7 mL) along with p-toluene sulfonic acid (100 mg, 0.53 mmole). This mixture was then stirred overnight. The reaction was quenched with triethylamine (0.10 mL, 0.72 mmole) and the solvents were removed in vacuo. The resulting residue was chromatographed with $CH_2Cl_2$/$Et_2O$ (2% v/v, $R_f$=0.14) to isolate the product (1.35 g, 95%). $^1H$ NMR δ7.72 (m, 3H, Np—H), 7.42 (dd, J=7.0, 7.4 Hz, 1H, Np—H), 7.31 (dd, J=7.4, 7.2 Hz, 1H, Np—H), 7.12 (m, 2H, Np—H), 4.05 (t, J=6.5 Hz, 2H, Np—OCH$_2$), 3.72 (m, 1H, —OCH), 3.65–3.40 (m, 8H, —OCH$_2$), 2.26 (t, J=6.0 Hz, 1H, —OH), 1.84 (m, 2H, Np—OCH$_2$CH$_2$), 1.59–1.15 (m, 42H, aliphatic CH$_2$), 0.88 (t, J=6.5 Hz, 3H, —CH$_3$). $^{13}C$ NMR δ157.02, 134.56, 129.25, 128.81, 127.58, 126.64, 126.23, 123.40, 118.98, 106.42, 78.22, 71.82, 70.85, 70.30, 67.88, 63.04, 31.92, 30.03, 29.70, 29.46, 29.37, 29.22, 26.051 22.69, 14.14. IR (KBr) 3420, 3060, 2918, 2849, 1629, 1600, 1470, 1218, 1120, 1051, 815, 742 cm$^{-1}$. Anal. Calcd for $C_{39}H_{66}O_4$: C, 78.21; H, 11.11. Found: C, 78.40, H, 10.89.

Preparation of 1-octacecyl-2(8-(naphthyl-2-oxy)-1-octyl)-rac-glycero-3-(8-(3,6-dioxy)-octan-1-ol(23) is shown as step "d" in FIG. 15. 22 (1.18 g, 1.97 mmole) was placed in 10 mL THF and syringed into a suspension of NaH (0.292 g of 60% oil dispersion, 7.30 mmole) in 10 mL THF. This mixture was stirred for 2 hours at room temperature. 15 (1.2 g, 2.57 mmole) was then added as a solid and the reaction mixture was refluxed overnight. The solution was cooled to room temperature and quenched with $H_2O$ (50 mL). This mixture was then diluted with 70 mL ethyl acetate. After shaking, the organic layer was taken and the aqueous layer was extracted twice with 70 mL ethyl acetate. The combined organics were then washed with water (50 mL) and aq. sat. NaCl solution (50 mL). The solution was dried over MgSO$_4$ and the solvent was removed in vacuo. The residue was taken up in THF (7 mL)/methanol (7 mL) and p-toluene sulfonic acid (100 mg, 0.53 mmole) was added. This mixture was stirred 15 hours and then quenched with triethylamine (0.10 mL, 0.72 mmole). The solvent was then removed in vacuo. The residue was chromatographed with ethyl acetate/hexanes (60% v/v, $R_f$=0.24) to isolate the product (1.34 g, 93%). $^1H$ NMR δ7.73 (m, 3H, Np—H), 7.42 (dd, J=6.9, 7.7 Hz, 1H, Np—H), 7.32 (dd, J=7.2, 7.8 Hz, 1H, Np—H), 7.15 (m, 2H, Np—H), 4.07 (t, J=6.5 Hz, 2H, Np—OCH$_2$), 3.74–3.41 (m, 21H, —OC(H)), 2.36 (br s, 1H, OH), 1.84 (m, 2H, Np—OCH$_2$CH$_2$), 1.57–1.25 (m, 42H, aliphatic CH$_2$), 0.88 (t, J=6.4 Hz, 3H, —CH$_3$). $^{13}C$ NMR δ157.01, 134.54, 129.21, 128.78, 127.54, 126.61, 126.19, 123.36, 118.95, 106.41, 77.81, 72.57, 71.61, 71.30, 70.72, 70.57, 70.50, 70.48, 70.25, 67.88, 31.88, 29.97, 29.66, 29.61, 29.46, 29.35, 29.19, 26.07, 26.03, 25.97, 22.64, 14.09. IR (neat) 3448, 2924, 2853, 1629, 1601, 1466, 1258, 1217, 1181, 1120, 836 cm$^{-1}$. Anal. Calcd for $C_{45}H_{78}O_7$: C, 73.93; H, 10.75. Found: C, 73.54; H, 10.89.

Preparation of 1-octacecyl-2-(8-(naphthyl-2-oxy)-1-octyl)-rac-glycero-3-(8-(3,6-dioxy)octyl-1-bromide) (24) is shown as step "e" in FIG. 15. 23 (1.11 g, 1.52 mmole) was dissolved in THF (10 mL) and stirred at 5° C. Carbon tetrabromide (1.01 g, 3.04 mmole) and triphenyl phosphine (0.80 g, 3.05 mmole) were added to the solution and the reaction was allowed to proceed with stirring for 17 hours. The solvent was then removed in vacuo and the residue was chromatographed with ethyl acetate/hexanes (20% v/v, $R_f$=0.22) to isolate the product (1.5 g, 95%). $^1H$ NMR δ7.73 (m, 3H, Np—H), 7.42 (dd, J=7.4, 7.5 Hz, 1H, Np—H), 7.32 (dd, J=7.5, 7.5 Hz, 1H, Np—H), 7.15 (m, 2H, Np—H), 4.06 (t, J=6.5 Hz, 2H, Np—OCH$_2$), 3.80 (t, J=6.3 Hz, 2H, —CH$_2$Br), 3.66–3.40 (m, 19H, —OCH), 1.84 (m, 2H, Np—OCH$_2$CH$_2$), 1.57–1.25 (m, 42H, aliphatic CH$_2$), 0.88 (t, J=6.6 Hz, 3H, —CH$_3$). $^{13}C$ NMR δ157.03, 134.56, 129.24, 128.81, 127.57, 126.63, 126.22, 123.39, 118.97, 106.43, 77.83, 71.63, 71.37, 71.17, 70.83, 70.67, 70.59, 70.57, 70.51, 67.91, 31.90, 30.25, 30.04, 29.68, 29.64, 29.49, 29.39, 29.35, 29.22, 26.11, 26.06, 26.01, 22.67, 14.12. IR (neat) 2924, 2853, 1630, 1601, 1465, 1258, 1217, 1181, 1119, 836 cm$^{-1}$. Anal. Calcd for $C_{45}H_{77}O_6Br$: C, 68.07; H, 9.77. Found: C, 68.07; H, 9.53.

Preparation of 1-octacecyl-2-(8-(naphthyl-2-oxy)-1-octyl)-rac-glycero-3-(8-(3,6-dioxy)octyl-1-diethylamino-N,N-diacetate) (25) is shown as step "f" in FIG. 15. 24 (0.60 g, 0.76 mmole), diethyliminodiacetate (0.57 g, 3.0 mmole) and triethylamine (0.303 g; 3.0 mmole) were placed in acetonitrile (10 mL)/THF (2 mL) and refluxed 22 hours. The solvent was removed in vacuo and the residue was chromatographed with ethyl acetate/hexanes (40% v/v, $R_f$=0.23) to isolate the product (0.31 g, 45%). $^1$H NMR δ7.73 (m, 3H, Np—H), 7.42 (dd, J=7.0, 7.2 Hz, 1H, Np—H), 7.31 (dd, J=7.4, 7.5 Hz, 1H, Np—H), 7.15 (m, 2H, Np—H), 4.15 (q, J=7.1 Hz, 4H, C(=O)OCH$_2$), 4.06 (t, J=6.5 Hz, 2H, Np—OCH$_2$), 3.62– 3.40 (m, 23H, —NCH$_2$C(=O), —OC(H)), 2.97 (t, J=5.6 Hz, 2H, —CH$_2$N), 1.84 (m, 2H, Np—OCH$_2$CH$_2$), 1.57–1.24 (m, 48H, C(=O)OCH$_2$CH$_3$, aliphatic CH$_2$), 0.88 (t, J=6.6 Hz, 3H, —CH$_3$). $^{13}$C NMR δ171.33, 157.05, 134.57, 129.25, 128.82, 127.58, 126.64, 126.23, 123.40, 118.99, 106.45, 77.83, 71.64, 71.37, 70.81, 70.74, 70.52, 70.31, 70.27, 67.94, 60.44, 55.82, 53.57, 31.91, 30.05, 29.69, 29.65, 29.50, 29.41, 29.30, 29.23, 26.11, 26.07, 26.02, 22.68, 14.24, 14.12. IR (neat) 3312, 2923, 2852, 1742, 1686, 1630, 1543, 1466, 1258, 1118, 836 cm$^{-1}$. Anal. Calcd for $C_{53}H_{91}N_{10}$: C, 70.55; H: 10.15; N: 1.55. Found C, 70.71; H, 10.34; N, 1.29.

Preparation of 1-octacecyl-2-(8-(naphthyl-2-oxy)-1-octyl)-rac-glycero-3-(8-(3,6-dioxy)octyl-1-amino-N,N-diacetic acid) (26, naphthyl stearyl iminodiacetic acid or NSIDA), is shown as step "g" in FIG. 15. 25 (0.26 g, 0.29 mmole) and NaOH (100 mg, 2.5 mmole) were placed in THF (5 mL)/methanol (5 mL)/water (2 mL) and refluxed for 1 hour. The solution was cooled to room temperature and acidified to pH 1. The solution was then concentrated in vacuo, during which a solid formed. The solid was taken up in Et$_2$O (70 mL) and 30 mL of aq. sat. NaCl solution was added. After shaking, the aqueous layer was separated and extracted twice with 45 mL Et$_2$O. The organic layers were combined and dried over anhydrous MgSO$_4$, filtered and the solvent was then removed in vacuo. The compound was taken up in a small amount of CH$_2$Cl$_2$ and passed through a small plug of silica gel. Excess solvent was removed under vacuo leaving a colorless waxy solid (0.11 g, 45%). $^1$H NMR δ7.74 (m, 3H, Np—H), 7.42 (dd, J=7.0, 7.2 Hz, 1H, Np—H), 7.31 (dd, J=7.4, 7.5 Hz, 1H, Np—H), 7.15 (m, 2H, Np—H), 6.03 (br s, 2H, —CO$_2$H), 4.06 (t, J=6.5 Hz, 2H, Np—OCH$_2$), 3.77 (br s, 2H, NCH$_2$CO$_2$H), 1.54 (m, 4H, CH$_2$CH$_2$O), 1.34 (m, 38H, aliphatic CH$_2$), 0.88 (t, J=6.6 Hz, 3H, —CH$_3$). $^{13}$C NMR δ171.19, 157.07, 134.59, 129.28, 128.83, 127.60, 126.68, 126.27, 123.43, 119.01, 106.49, 78.05, 71.76, 71.28, 71.04, 70.53, 70.46, 70.34, 70.23, 68.09, 67.96, 57.75, 55.48, 31.94, 29.97, 29.73, 29.53, 29.40, 29.25, 26.10, 26.00, 22.71, 14.15. IR (neat) 3422, 2923, 2853, 1731, 1630, 1601, 1466, 1390, 1390, 1258, 1217, 1181, 1119, 835 cm$^{-1}$. Anal. Calcd for $C_{49}H_{85}NO_{10}$: C, 68.10; H, 9.91; N, 1.62. Found: C, 67.84; H, 9.81; N, 1.32.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A lipid-based sensor for use in detecting the presence of a metal ion, said sensor exhibiting a change in fluorescence when said sensor is exposed to said metal ion, said sensor comprising:

A matrix lipid comprising at least one lipid layer, said lipid layer having a hydrophobic interior region and a hydrophilic outer surface;

a plurality of fluorescent metal-chelating amphiphiles incorporated in said lipid layer, each of said fluorescent metal-chelating amphiphiles having the structure:

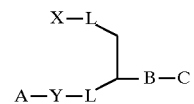

configuration a or

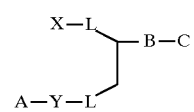

configuration b wherein A is a hydrophobic fluorophore, X is an aliphatic hydrocarbon having from 18 to 20 carbon atoms and Y is an aliphatic hydrocarbon having from 9 to 11 carbon atoms, B is cysteine, glycine, cysteamine or $C_nH_{2n}O_n$ where n=2–10, C is a metal chelator selected from the group consisting of iminodiacetic acid, cyclam, penicillamine, dimercaptosuccinic acid, tartrate, thiomalic acid, crown ethers, nitrolotriacetatic acid, ethylenediamine-tetraacetic acid, ethylenebis(oxyethylenenitrilo)tetraacetic acid, 3,6-dioxaoctanedithioamide, 3,6-dioxaoctanediamide, salicyladoximine, dithiooxamide, 8-hydroxyguinoline, cupferron, 2,2'-thiobis(ethyl acetoacetate), 2,2'-dipyridyl, and L is either an ether or ester linkage.

2. A lipid-based sensor according to claim 1 wherein said lipid anchor comprises a bilayer liposome.

3. A lipid-based sensor according to claim 1 wherein A is a fluorophores selected from the group consisting of pyrene, anthracene, naphthalene and phenanthrene.

4. A lipid-based sensor according to claim 3 wherein said fluorophore is pyrene or naphthalene.

5. A lipid-based sensor according to claim 1 wherein C is iminodiacetic acid.

6. A lipid-based sensor according to claim 3 wherein C is iminodiacetic acid.

7. A lipid-based sensor according to claim 1 wherein A is pyrene.

8. A lipid based metal sensor according to claim 1 wherein X is $CH_3(CH_2)_{17}$ and Y is $(CH_2)_9$.

9. A lipid based metal sensor according to claim 1 wherein L is an ether linkage.

10. A lipid based metal sensor according to claim 1 wherein B is $(OCH_2CH_2)_3$.

11. A lipid based metal sensor according to claim 8 wherein A is pyrene, B is $(OCH_2CH_2)_3$, L is an ether linkage and C is iminodiacetic acid.

12. A lipid based metal sensor according to claim 11 wherein said fluorescent metal-chelating amphiphile has the structure of configuration A.

* * * * *